US012790363B2

(12) United States Patent
Benner et al.

(10) Patent No.: US 12,790,363 B2
(45) **Date of Patent: *Nov. 10, 2026**

(54) NUCLEOTIDE ANALOGS FOR EFFICIENT DNA AND RNA AMPLIFICATION

(71) Applicant: FIREBIRD DIAGNOTICS, Alachua, FL (US)

(72) Inventors: Steven A. Benner, Gainesville, FL (US); Zunyi Yang, Gainesville, FL (US); Myong Jung Kim, Gainesville, FL (US)

(73) Assignee: FIREBIRD DIAGNOTICS, Alachua, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/188,592

(22) Filed: Apr. 24, 2025

(65) Prior Publication Data

US 2026/0347385 A1 Nov. 5, 2026

(51) Int. Cl.
*C07H 21/04* (2006.01)
*C07D 405/04* (2006.01)

(52) U.S. Cl.
CPC .......... *C07H 21/04* (2013.01); *C07D 405/04* (2013.01)

(58) Field of Classification Search
CPC ....... C07H 21/00; C07H 21/04; C07D 405/04
See application file for complete search history.

(56) References Cited

U.S. PATENT DOCUMENTS 6,447,998 B1 * 9/2002 Froehler ................ C07H 19/00 435/6.12
8,053,212 B1 * 11/2011 Benner ................ C07D 405/04 546/264

OTHER PUBLICATIONS

Walter et al., Nucleic Acids Research, 2018, 46(16), p. 8069-8078. (Year: 2018).*

* cited by examiner

*Primary Examiner* — Jonathan S Lau
(74) *Attorney, Agent, or Firm* — SALIWANCHIK, LLOYD & EISENSCHENK

(57) ABSTRACT

This invention covers DNA analogs and processes that amplify many dozens to hundreds of DNA and RNA targets, solving the "multiplexed PCR problem" as well as supporting isothermal amplification and delivering other capabilities in multiplexed molecular analysis.

31 Claims, 11 Drawing Sheets

Specification includes a Sequence Listing.

9 10 11 12 13 14 15 16 17

18

19

20a

+

20b

21

22

18 23 24 25 26

18 19a 18 19a

SEQUENCE LISTING

```
Sequence total quantity: 145
SEQ ID NO: 1              moltype = DNA  length = 14
FEATURE                   Location/Qualifiers
source                    1..14
                          mol_type = unassigned DNA
                          note = synthetic construct
                          organism = unidentified

SEQUENCE: 1
tctggcggac actg                                                      14
```

-continued

```
SEQ ID NO: 2            moltype = DNA  length = 14
FEATURE                 Location/Qualifiers
source                  1..14
                        mol_type = unassigned DNA
                        note = synthetic construct
                        organism = unidentified
SEQUENCE: 2
cagtgtccgt caga                                                            14

SEQ ID NO: 3            moltype = DNA  length = 14
FEATURE                 Location/Qualifiers
source                  1..14
                        mol_type = unassigned DNA
                        note = synthetic construct
                        organism = unidentified
modified_base           5
                        mod_base = OTHER
                        note = inosine
SEQUENCE: 3
tctggcggac actg                                                            14

SEQ ID NO: 4            moltype = DNA  length = 14
FEATURE                 Location/Qualifiers
source                  1..14
                        mol_type = unassigned DNA
                        note = synthetic construct
                        organism = unidentified
SEQUENCE: 4
tctgccggac actg                                                            14

SEQ ID NO: 5            moltype = DNA  length = 14
FEATURE                 Location/Qualifiers
source                  1..14
                        mol_type = unassigned DNA
                        note = synthetic construct
                        organism = unidentified
SEQUENCE: 5
tctgtcggac actg                                                            14

SEQ ID NO: 6            moltype = DNA  length = 14
FEATURE                 Location/Qualifiers
source                  1..14
                        mol_type = unassigned DNA
                        note = synthetic construct
                        organism = unidentified
SEQUENCE: 6
ggggttggag actg                                                            14

SEQ ID NO: 7            moltype = DNA  length = 14
FEATURE                 Location/Qualifiers
source                  1..14
                        mol_type = unassigned DNA
                        note = synthetic construct
                        organism = unidentified
SEQUENCE: 7
cagtctccaa cctc                                                            14

SEQ ID NO: 8            moltype = DNA  length = 14
FEATURE                 Location/Qualifiers
source                  1..14
                        mol_type = unassigned DNA
                        note = synthetic construct
                        organism = unidentified
modified_base           2
                        mod_base = OTHER
                        note = inosine
SEQUENCE: 8
ggggttggag actg                                                            14

SEQ ID NO: 9            moltype = DNA  length = 14
FEATURE                 Location/Qualifiers
source                  1..14
                        mol_type = unassigned DNA
                        note = synthetic construct
                        organism = unidentified
SEQUENCE: 9
gcggttggag actg                                                            14
```

-continued

```
SEQ ID NO: 10          moltype = DNA  length = 14
FEATURE                Location/Qualifiers
source                 1..14
                       mol_type = unassigned DNA
                       note = synthetic construct
                       organism = unidentified
SEQUENCE: 10
gtggttggag actg                                                            14

SEQ ID NO: 11          moltype = DNA  length = 14
FEATURE                Location/Qualifiers
source                 1..14
                       mol_type = unassigned DNA
                       note = synthetic construct
                       organism = unidentified
SEQUENCE: 11
ctggctggag actg                                                            14

SEQ ID NO: 12          moltype = DNA  length = 14
FEATURE                Location/Qualifiers
source                 1..14
                       mol_type = unassigned DNA
                       note = synthetic construct
                       organism = unidentified
SEQUENCE: 12
cagtctccag tcag                                                            14

SEQ ID NO: 13          moltype = DNA  length = 14
FEATURE                Location/Qualifiers
source                 1..14
                       mol_type = unassigned DNA
                       note = synthetic construct
                       organism = unidentified
modified_base          4
                       mod_base = OTHER
                       note = inosine
SEQUENCE: 13
ctggctggag actg                                                            14

SEQ ID NO: 14          moltype = DNA  length = 14
FEATURE                Location/Qualifiers
source                 1..14
                       mol_type = unassigned DNA
                       note = Synthetic construct
                       organism = unidentified
SEQUENCE: 14
ctgcctggag actg                                                            14

SEQ ID NO: 15          moltype = DNA  length = 14
FEATURE                Location/Qualifiers
source                 1..14
                       mol_type = unassigned DNA
                       note = Synthetic construct
                       organism = unidentified
SEQUENCE: 15
ctgtctggag actg                                                            14

SEQ ID NO: 16          moltype = DNA  length = 14
FEATURE                Location/Qualifiers
source                 1..14
                       mol_type = unassigned DNA
                       note = Synthetic construct
                       organism = unidentified
modified_base          10
                       mod_base = OTHER
                       note =
                        3-(1-propynyl)-5-(1'-beta-D-2'-deoxyribofuranosyl)-pyrid-2-
                        one
SEQUENCE: 16
cagtgtccgt caga                                                            14

SEQ ID NO: 17          moltype = DNA  length = 14
FEATURE                Location/Qualifiers
source                 1..14
                       mol_type = unassigned DNA
                       note = Synthetic construct
                       organism = unidentified
modified_base          13
                       mod_base = OTHER
```

-continued

```
                         note =
                          3-(1-propynyl)-5-(1'-beta-D-2'-deoxyribofuranosyl)-pyrid-2-
                          one
SEQUENCE: 17
cagtctccaa cctc                                                    14

SEQ ID NO: 18            moltype = DNA  length = 14
FEATURE                  Location/Qualifiers
source                   1..14
                         mol_type = unassigned DNA
                         note = Synthetic construct
                         organism = unidentified
modified_base            11
                         mod_base = OTHER
                         note =
                          3-(1-propynyl)-5-(1'-beta-D-2'-deoxyribofuranosyl)-pyrid-2-
                          one
SEQUENCE: 18
cagtctccag tcag                                                    14

SEQ ID NO: 19            moltype = DNA  length = 14
FEATURE                  Location/Qualifiers
source                   1..14
                         mol_type = unassigned DNA
                         note = Synthetic construct
                         organism = unidentified
modified_base            13
                         mod_base = OTHER
                         note =
                          3-(1-propynyl)-5-(1'-beta-D-2'-deoxyribofuranosyl)-pyrid-2-
                          one
SEQUENCE: 19
cagtcagcac agta                                                    14

SEQ ID NO: 20            moltype = DNA  length = 14
FEATURE                  Location/Qualifiers
source                   1..14
                         mol_type = unassigned DNA
                         note = Synthetic construct
                         organism = unidentified
modified_base            10
                         mod_base = OTHER
                         note =
                          3-(1-propynyl)-5-(1'-beta-D-2'-deoxyribofuranosyl)-pyrid-2-
                          one
SEQUENCE: 20
cagtcagcat agcg                                                    14

SEQ ID NO: 21            moltype = DNA  length = 14
FEATURE                  Location/Qualifiers
source                   1..14
                         mol_type = unassigned DNA
                         note = Synthetic construct
                         organism = unidentified
modified_base            11
                         mod_base = OTHER
                         note =
                          3-(1-propynyl)-5-(1'-beta-D-2'-deoxyribofuranosyl)-pyrid-2-
                          one
SEQUENCE: 21
cagtcagcaa tcgg                                                    14

SEQ ID NO: 22            moltype = DNA  length = 14
FEATURE                  Location/Qualifiers
source                   1..14
                         mol_type = unassigned DNA
                         note = Synthetic construct
                         organism = unidentified
modified_base            13
                         mod_base = OTHER
                         note =
                          3-(1-propynyl)-5-(1'-beta-D-2'-deoxyribofuranosyl)-pyrid-2-
                          one
SEQUENCE: 22
cagtcagcca agtt                                                    14

SEQ ID NO: 23            moltype = DNA  length = 14
FEATURE                  Location/Qualifiers
source                   1..14
```

-continued

```
                        mol_type = unassigned DNA
                        note = Synthetic construct
                        organism = unidentified
modified_base           10
                        mod_base = OTHER
                        note =
                         3-(1-propynyl)-5-(1'-beta-D-2'-deoxyribofuranosyl)-pyrid-2-
                         one
SEQUENCE: 23
cactctgctt ggct                                                              14

SEQ ID NO: 24           moltype = DNA  length = 14
FEATURE                 Location/Qualifiers
source                  1..14
                        mol_type = unassigned DNA
                        note = Synthetic construct
                        organism = unidentified
modified_base           10
                        mod_base = OTHER
                        note =
                         3-(1-propynyl)-5-(1'-beta-D-2'-deoxyribofuranosyl)-pyrid-2-
                         one
SEQUENCE: 24
cactctgcct tgaa                                                              14

SEQ ID NO: 25           moltype = DNA  length = 14
FEATURE                 Location/Qualifiers
source                  1..14
                        mol_type = unassigned DNA
                        note = Synthetic construct
                        organism = unidentified
SEQUENCE: 25
tctgacggac actg                                                              14

SEQ ID NO: 26           moltype = DNA  length = 14
FEATURE                 Location/Qualifiers
source                  1..14
                        mol_type = unassigned DNA
                        note = Synthetic construct
                        organism = unidentified
SEQUENCE: 26
gaggttggag actg                                                              14

SEQ ID NO: 27           moltype = DNA  length = 14
FEATURE                 Location/Qualifiers
source                  1..14
                        mol_type = unassigned DNA
                        note = Synthetic construct
                        organism = unidentified
SEQUENCE: 27
ctgactggag actg                                                              14

SEQ ID NO: 28           moltype = DNA  length = 14
FEATURE                 Location/Qualifiers
source                  1..14
                        mol_type = unassigned DNA
                        note = Synthetic construct
                        organism = unidentified
SEQUENCE: 28
tactgtgctg actg                                                              14

SEQ ID NO: 29           moltype = DNA  length = 14
FEATURE                 Location/Qualifiers
source                  1..14
                        mol_type = unassigned DNA
                        note = Synthetic construct
                        organism = unidentified
SEQUENCE: 29
cgctatgctg actg                                                              14

SEQ ID NO: 30           moltype = DNA  length = 14
FEATURE                 Location/Qualifiers
source                  1..14
                        mol_type = unassigned DNA
                        note = Synthetic construct
                        organism = unidentified
SEQUENCE: 30
ccgattgctg actg                                                              14
```

-continued

```
SEQ ID NO: 31          moltype = DNA  length = 14
FEATURE                Location/Qualifiers
source                 1..14
                       mol_type = unassigned DNA
                       note = Synthetic construct
                       organism = unidentified
SEQUENCE: 31
aacttggctg actg                                                      14

SEQ ID NO: 32          moltype = DNA  length = 14
FEATURE                Location/Qualifiers
source                 1..14
                       mol_type = unassigned DNA
                       note = Synthetic construct
                       organism = unidentified
SEQUENCE: 32
agccaagcag agtg                                                      14

SEQ ID NO: 33          moltype = DNA  length = 14
FEATURE                Location/Qualifiers
source                 1..14
                       mol_type = unassigned DNA
                       note = Synthetic construct
                       organism = unidentified
SEQUENCE: 33
ttcaaggcag agtg                                                      14

SEQ ID NO: 34          moltype = DNA  length = 14
FEATURE                Location/Qualifiers
source                 1..14
                       mol_type = unassigned DNA
                       note = Synthetic construct
                       organism = unidentified
modified_base          5
                       mod_base = OTHER
                       note = 2-aminopurine
SEQUENCE: 34
tctgacggac actg                                                      14

SEQ ID NO: 35          moltype = DNA  length = 14
FEATURE                Location/Qualifiers
source                 1..14
                       mol_type = unassigned DNA
                       note = Synthetic construct
                       organism = unidentified
modified_base          2
                       mod_base = OTHER
                       note = 2-aminopurine
SEQUENCE: 35
gaggttggag actg                                                      14

SEQ ID NO: 36          moltype = DNA  length = 14
FEATURE                Location/Qualifiers
source                 1..14
                       mol_type = unassigned DNA
                       note = Synthetic construct
                       organism = unidentified
modified_base          4
                       mod_base = OTHER
                       note = 2-aminopurine
SEQUENCE: 36
ctgactggag actg                                                      14

SEQ ID NO: 37          moltype = DNA  length = 14
FEATURE                Location/Qualifiers
source                 1..14
                       mol_type = unassigned DNA
                       note = Synthetic construct
                       organism = unidentified
modified_base          2
                       mod_base = OTHER
                       note = 2-aminopurine
SEQUENCE: 37
tactgtgctg actg                                                      14

SEQ ID NO: 38          moltype = DNA  length = 14
FEATURE                Location/Qualifiers
source                 1..14
                       mol_type = unassigned DNA
```

-continued

```
                        note = Synthetic construct
                        organism = unidentified
SEQUENCE: 38
cagtcagcac agta                                                 14

SEQ ID NO: 39           moltype = DNA  length = 14
FEATURE                 Location/Qualifiers
source                  1..14
                        mol_type = unassigned DNA
                        note = Synthetic construct
                        organism = unidentified
modified_base           5
                        mod_base = OTHER
                        note = 2-aminopurine
SEQUENCE: 39
cgctatgctg actg                                                 14

SEQ ID NO: 40           moltype = DNA  length = 14
FEATURE                 Location/Qualifiers
source                  1..14
                        mol_type = unassigned DNA
                        note = Synthetic construct
                        organism = unidentified
SEQUENCE: 40
cagtcagcat agcg                                                 14

SEQ ID NO: 41           moltype = DNA  length = 14
FEATURE                 Location/Qualifiers
source                  1..14
                        mol_type = unassigned DNA
                        note = Synthetic construct
                        organism = unidentified
modified_base           4
                        mod_base = OTHER
                        note = 2-aminopurine
SEQUENCE: 41
ccgattgctg actg                                                 14

SEQ ID NO: 42           moltype = DNA  length = 14
FEATURE                 Location/Qualifiers
source                  1..14
                        mol_type = unassigned DNA
                        note = Synthetic construct
                        organism = unidentified
SEQUENCE: 42
cagtcagcaa tcgg                                                 14

SEQ ID NO: 43           moltype = DNA  length = 14
FEATURE                 Location/Qualifiers
source                  1..14
                        mol_type = unassigned DNA
                        note = Synthetic construct
                        organism = unidentified
modified_base           2
                        mod_base = OTHER
                        note = 2-aminopurine
SEQUENCE: 43
aacttggctg actg                                                 14

SEQ ID NO: 44           moltype = DNA  length = 14
FEATURE                 Location/Qualifiers
source                  1..14
                        mol_type = unassigned DNA
                        note = Synthetic construct
                        organism = unidentified
SEQUENCE: 44
cagtcagcca agtt                                                 14

SEQ ID NO: 45           moltype = DNA  length = 14
FEATURE                 Location/Qualifiers
source                  1..14
                        mol_type = unassigned DNA
                        note = Synthetic construct
                        organism = unidentified
modified_base           5
                        mod_base = OTHER
                        note = 2-aminopurine
SEQUENCE: 45
agccaagcag agtg                                                 14
```

```
SEQ ID NO: 46           moltype = DNA  length = 14
FEATURE                 Location/Qualifiers
source                  1..14
                        mol_type = unassigned DNA
                        note = synthetic construct
                        organism = unidentified
SEQUENCE: 46
cactctgctt ggct                                                     14

SEQ ID NO: 47           moltype = DNA  length = 14
FEATURE                 Location/Qualifiers
source                  1..14
                        mol_type = unassigned DNA
                        note = synthetic construct
                        organism = unidentified
modified_base           5
                        mod_base = OTHER
                        note = 2-aminopurine
SEQUENCE: 47
ttcaaggcag agtg                                                     14

SEQ ID NO: 48           moltype = DNA  length = 14
FEATURE                 Location/Qualifiers
source                  1..14
                        mol_type = unassigned DNA
                        note = synthetic construct
                        organism = unidentified
SEQUENCE: 48
cactctgcct tgaa                                                     14

SEQ ID NO: 49           moltype = DNA  length = 15
FEATURE                 Location/Qualifiers
source                  1..15
                        mol_type = unassigned DNA
                        note = synthetic construct
                        organism = unidentified
SEQUENCE: 49
accaagctat caagt                                                    15

SEQ ID NO: 50           moltype = DNA  length = 15
FEATURE                 Location/Qualifiers
source                  1..15
                        mol_type = unassigned DNA
                        note = synthetic construct
                        organism = unidentified
modified_base           8
                        mod_base = OTHER
                        note = 2-thiothymidine
SEQUENCE: 50
accaagctat caagt                                                    15

SEQ ID NO: 51           moltype = DNA  length = 15
FEATURE                 Location/Qualifiers
source                  1..15
                        mol_type = unassigned DNA
                        note = synthetic construct
                        organism = unidentified
SEQUENCE: 51
accaagcaat caagt                                                    15

SEQ ID NO: 52           moltype = DNA  length = 15
FEATURE                 Location/Qualifiers
source                  1..15
                        mol_type = unassigned DNA
                        note = synthetic construct
                        organism = unidentified
modified_base           8
                        mod_base = OTHER
                        note = 2-aminopurine
SEQUENCE: 52
accaagcaat caagt                                                    15

SEQ ID NO: 53           moltype = DNA  length = 15
FEATURE                 Location/Qualifiers
source                  1..15
                        mol_type = unassigned DNA
                        note = synthetic construct
                        organism = unidentified
```

-continued

```
SEQUENCE: 53
accaagccat caagt                                                  15

SEQ ID NO: 54         moltype = DNA  length = 15
FEATURE               Location/Qualifiers
source                1..15
                      mol_type = unassigned DNA
                      note = synthetic construct
                      organism = unidentified
modified_base         8
                      mod_base = OTHER
                      note = N-ethylcytidine
SEQUENCE: 54
accaagccat caagt                                                  15

SEQ ID NO: 55         moltype = DNA  length = 15
FEATURE               Location/Qualifiers
source                1..15
                      mol_type = unassigned DNA
                      note = synthetic construct
                      organism = unidentified
SEQUENCE: 55
accaagcgat caagt                                                  15

SEQ ID NO: 56         moltype = DNA  length = 15
FEATURE               Location/Qualifiers
source                1..15
                      mol_type = unassigned DNA
                      note = synthetic construct
                      organism = unidentified
modified_base         8
                      mod_base = OTHER
                      note = inosine
SEQUENCE: 56
accaagcgat caagt                                                  15

SEQ ID NO: 57         moltype = DNA  length = 15
FEATURE               Location/Qualifiers
source                1..15
                      mol_type = unassigned DNA
                      note = synthetic construct
                      organism = unidentified
SEQUENCE: 57
acttgattgc ttggt                                                  15

SEQ ID NO: 58         moltype = DNA  length = 15
FEATURE               Location/Qualifiers
source                1..15
                      mol_type = unassigned DNA
                      note = synthetic construct
                      organism = unidentified
modified_base         8
                      mod_base = OTHER
                      note = 2-thiothymidine
SEQUENCE: 58
acttgattgc ttggt                                                  15

SEQ ID NO: 59         moltype = DNA  length = 15
FEATURE               Location/Qualifiers
source                1..15
                      mol_type = unassigned DNA
                      note = synthetic construct
                      organism = unidentified
SEQUENCE: 59
acttgatagc ttggt                                                  15

SEQ ID NO: 60         moltype = DNA  length = 15
FEATURE               Location/Qualifiers
source                1..15
                      mol_type = unassigned DNA
                      note = synthetic construct
                      organism = unidentified
modified_base         8
                      mod_base = OTHER
                      note = 2-aminopurine
SEQUENCE: 60
acttgatagc ttggt                                                  15

SEQ ID NO: 61         moltype = DNA  length = 15
```

-continued

```
FEATURE               Location/Qualifiers
source                1..15
                      mol_type = unassigned DNA
                      note = synthetic construct
                      organism = unidentified
SEQUENCE: 61
acttgatcgc ttggt                                                    15

SEQ ID NO: 62         moltype = DNA  length = 15
FEATURE               Location/Qualifiers
source                1..15
                      mol_type = unassigned DNA
                      note = synthetic construct
                      organism = unidentified
modified_base         8
                      mod_base = OTHER
                      note = N-ethylcytidine
SEQUENCE: 62
acttgatcgc ttggt                                                    15

SEQ ID NO: 63         moltype = DNA  length = 15
FEATURE               Location/Qualifiers
source                1..15
                      mol_type = unassigned DNA
                      note = synthetic construct
                      organism = unidentified
SEQUENCE: 63
acttgatggc ttggt                                                    15

SEQ ID NO: 64         moltype = DNA  length = 15
FEATURE               Location/Qualifiers
source                1..15
                      mol_type = unassigned DNA
                      note = synthetic construct
                      organism = unidentified
modified_base         8
                      mod_base = OTHER
                      note = inosine
SEQUENCE: 64
acttgatggc ttggt                                                    15

SEQ ID NO: 65         moltype = DNA  length = 15
FEATURE               Location/Qualifiers
source                1..15
                      mol_type = unassigned DNA
                      note = synthetic construct
                      organism = unidentified
modified_base         8
                      mod_base = OTHER
                      note =
                       3-(1-propynyl)-5-(1'-beta-D-2'-deoxyribofuranosyl)-pyrid-2-
                       one
SEQUENCE: 65
accaagctat caagt                                                    15

SEQ ID NO: 66         moltype = DNA  length = 15
FEATURE               Location/Qualifiers
source                1..15
                      mol_type = unassigned DNA
                      note = synthetic construct
                      organism = unidentified
modified_base         8
                      mod_base = OTHER
                      note =
                       3-(1-propynyl)-5-(1'-beta-D-2'-deoxyribofuranosyl)-pyrid-2-
                       one
SEQUENCE: 66
acttgattgc ttggt                                                    15

SEQ ID NO: 67         moltype = DNA  length = 20
FEATURE               Location/Qualifiers
source                1..20
                      mol_type = unassigned DNA
                      note = synthetic construct
                      organism = unidentified
SEQUENCE: 67
agaactccag gtgcttgtcc                                               20

SEQ ID NO: 68         moltype = DNA  length = 21
```

-continued

```
FEATURE                 Location/Qualifiers
source                  1..21
                        mol_type = unassigned DNA
                        note = synthetic construct
                        organism = unidentified
SEQUENCE: 68
cctctctcct agctctggac a                                      21

SEQ ID NO: 69           moltype = DNA  length = 28
FEATURE                 Location/Qualifiers
source                  1..28
                        mol_type = unassigned DNA
                        note = synthetic construct
                        organism = unidentified
SEQUENCE: 69
gtgattttga gaaatctttc ctttgagg                               28

SEQ ID NO: 70           moltype = DNA  length = 20
FEATURE                 Location/Qualifiers
source                  1..20
                        mol_type = unassigned DNA
                        note = synthetic construct
                        organism = unidentified
SEQUENCE: 70
ggtacaggga gaggagcctc                                        20

SEQ ID NO: 71           moltype = DNA  length = 20
FEATURE                 Location/Qualifiers
source                  1..20
                        mol_type = unassigned DNA
                        note = synthetic construct
                        organism = unidentified
modified_base           18
                        mod_base = OTHER
                        note = 2-thiothymidine
SEQUENCE: 71
agaactccag gtgcttgtcc                                        20

SEQ ID NO: 72           moltype = DNA  length = 20
FEATURE                 Location/Qualifiers
source                  1..20
                        mol_type = unassigned DNA
                        note = synthetic construct
                        organism = unidentified
modified_base           18
                        mod_base = OTHER
                        note =
                         3-(1-propynyl)-5-(1'-beta-D-2'-deoxyribofuranosyl)-pyrid-2-
                         one
SEQUENCE: 72
agaactccag gtgcttgtcc                                        20

SEQ ID NO: 73           moltype = DNA  length = 21
FEATURE                 Location/Qualifiers
source                  1..21
                        mol_type = unassigned DNA
                        note = synthetic construct
                        organism = unidentified
modified_base           19
                        mod_base = OTHER
                        note = 2-aminopurine
SEQUENCE: 73
cctctctcct agctctggac a                                      21

SEQ ID NO: 74           moltype = DNA  length = 28
FEATURE                 Location/Qualifiers
source                  1..28
                        mol_type = unassigned DNA
                        note = synthetic construct
                        organism = unidentified
modified_base           26
                        mod_base = OTHER
                        note = 2-aminopurine
SEQUENCE: 74
gtgattttga gaaatctttc ctttgagg                               28

SEQ ID NO: 75           moltype = DNA  length = 20
FEATURE                 Location/Qualifiers
source                  1..20
```

```
                         mol_type = unassigned DNA
                         note = synthetic construct
                         organism = unidentified
modified_base            19
                         mod_base = OTHER
                         note = 2-thiothymidine
SEQUENCE: 75
ggtacaggga gaggagcctc                                           20

SEQ ID NO: 76            moltype = DNA  length = 20
FEATURE                  Location/Qualifiers
source                   1..20
                         mol_type = unassigned DNA
                         note = synthetic construct
                         organism = unidentified
modified_base            19
                         mod_base = OTHER
                         note =
                          3-(1-propynyl)-5-(1'-beta-D-2'-deoxyribofuranosyl)-pyrid-2-
                          one
SEQUENCE: 76
ggtacaggga gaggagcctc                                           20

SEQ ID NO: 77            moltype = DNA  length = 17
FEATURE                  Location/Qualifiers
source                   1..17
                         mol_type = unassigned DNA
                         note = synthetic construct
                         organism = unidentified
SEQUENCE: 77
ccagatgcct ggctccg                                              17

SEQ ID NO: 78            moltype = DNA  length = 75
FEATURE                  Location/Qualifiers
source                   1..75
                         mol_type = unassigned DNA
                         note = synthetic construct
                         organism = unidentified
SEQUENCE: 78
ccagatgcct ggctccgcgt ataacactag ccatccttac tgcgcttcgg actctctccg  60
agcctcttca aaggc                                                75

SEQ ID NO: 79            moltype = DNA  length = 20
FEATURE                  Location/Qualifiers
source                   1..20
                         mol_type = unassigned DNA
                         note = synthetic construct
                         organism = unidentified
SEQUENCE: 79
gcctttgaag aggctcggag                                           20

SEQ ID NO: 80            moltype = DNA  length = 26
FEATURE                  Location/Qualifiers
source                   1..26
                         mol_type = unassigned DNA
                         note = synthetic construct
                         organism = unidentified
SEQUENCE: 80
acactagcca tccttactgc gcttcg                                    26

SEQ ID NO: 81            moltype = DNA  length = 86
FEATURE                  Location/Qualifiers
source                   1..86
                         mol_type = unassigned DNA
                         note = synthetic construct
                         organism = unidentified
SEQUENCE: 81
gtgattttga gaaatctttc ctttgaggcg tataacacta gccatcctta ctgcgcttcg  60
gactctgagg ctcctctccc tgtacc                                    86

SEQ ID NO: 82            moltype = DNA  length = 31
FEATURE                  Location/Qualifiers
source                   1..31
                         mol_type = unassigned DNA
                         note = synthetic construct
                         organism = unidentified
SEQUENCE: 82
gccttaaaga aataaaatga ctatgtgcag a                              31
```

-continued

```
SEQ ID NO: 83          moltype = DNA  length = 92
FEATURE                Location/Qualifiers
source                 1..92
                       mol_type = unassigned DNA
                       note = synthetic construct
                       organism = unidentified
SEQUENCE: 83
gccttaaaga aataaaatga ctatgtgcag acgtataaca ctagccatcc ttactgcgct  60
tcggactctc agactttgct ggagtttcaa gc                                92

SEQ ID NO: 84          moltype = DNA  length = 23
FEATURE                Location/Qualifiers
source                 1..23
                       mol_type = unassigned DNA
                       note = synthetic construct
                       organism = unidentified
SEQUENCE: 84
gcttgaaact ccagcaaagt ctg                                          23

SEQ ID NO: 85          moltype = DNA  length = 24
FEATURE                Location/Qualifiers
source                 1..24
                       mol_type = unassigned DNA
                       note = synthetic construct
                       organism = unidentified
SEQUENCE: 85
cttcttcctc ctcgtcatca tcat                                         24

SEQ ID NO: 86          moltype = DNA  length = 81
FEATURE                Location/Qualifiers
source                 1..81
                       mol_type = unassigned DNA
                       note = synthetic construct
                       organism = unidentified
SEQUENCE: 86
cttcttcctc ctcgtcatca tcattgttgt aacatcccag gcaattgctt gtcaaattag  60
ccatcatggc ctatcggggt c                                            81

SEQ ID NO: 87          moltype = DNA  length = 20
FEATURE                Location/Qualifiers
source                 1..20
                       mol_type = unassigned DNA
                       note = synthetic construct
                       organism = unidentified
SEQUENCE: 87
gaccccgata ggccatgatg                                              20

SEQ ID NO: 88          moltype = DNA  length = 23
FEATURE                Location/Qualifiers
source                 1..23
                       mol_type = unassigned DNA
                       note = synthetic construct
                       organism = unidentified
SEQUENCE: 88
acatcccagg caattgcttg tca                                          23

SEQ ID NO: 89          moltype = DNA  length = 17
FEATURE                Location/Qualifiers
source                 1..17
                       mol_type = unassigned DNA
                       note = synthetic construct
                       organism = unidentified
modified_base          14
                       mod_base = OTHER
                       note =
                        3-(1-propynyl)-5-(1'-beta-D-2'-deoxyribofuranosyl)-pyrid-2-
                        one
SEQUENCE: 89
ccagatgcct ggctccg                                                 17

SEQ ID NO: 90          moltype = DNA  length = 17
FEATURE                Location/Qualifiers
source                 1..17
                       mol_type = unassigned DNA
                       note = synthetic construct
                       organism = unidentified
modified_base          15
                       mod_base = OTHER
                       note = N-ethylcytidine
```

-continued

```
SEQUENCE: 90
ccagatgcct ggctccg                                                  17

SEQ ID NO: 91          moltype = DNA  length = 20
FEATURE                Location/Qualifiers
source                 1..20
                       mol_type = unassigned DNA
                       note = synthetic construct
                       organism = unidentified
modified_base          19
                       mod_base = OTHER
                       note = 2-aminopurine
SEQUENCE: 91
gcctttgaag aggctcggag                                               20

SEQ ID NO: 92          moltype = DNA  length = 20
FEATURE                Location/Qualifiers
source                 1..20
                       mol_type = unassigned DNA
                       note = synthetic construct
                       organism = unidentified
modified_base          18
                       mod_base = OTHER
                       note = inosine
SEQUENCE: 92
gcctttgaag aggctcggag                                               20

SEQ ID NO: 93          moltype = DNA  length = 24
FEATURE                Location/Qualifiers
source                 1..24
                       mol_type = unassigned DNA
                       note = synthetic construct
                       organism = unidentified
modified_base          20
                       mod_base = OTHER
                       note = 2-aminopurine
modified_base          23
                       mod_base = OTHER
                       note = 2-aminopurine
SEQUENCE: 93
cttcttcctc ctcgtcatca tcat                                          24

SEQ ID NO: 94          moltype = DNA  length = 24
FEATURE                Location/Qualifiers
source                 1..24
                       mol_type = unassigned DNA
                       note = synthetic construct
                       organism = unidentified
modified_base          21
                       mod_base = OTHER
                       note =
                        3-(1-propynyl)-5-(1'-beta-D-2'-deoxyribofuranosyl)-pyrid-2-
                        one
modified_base          23
                       mod_base = OTHER
                       note = 2-aminopurine
SEQUENCE: 94
cttcttcctc ctcgtcatca tcat                                          24

SEQ ID NO: 95          moltype = DNA  length = 24
FEATURE                Location/Qualifiers
source                 1..24
                       mol_type = unassigned DNA
                       note = synthetic construct
                       organism = unidentified
modified_base          21
                       mod_base = OTHER
                       note =
                        3-(1-propynyl)-5-(1'-beta-D-2'-deoxyribofuranosyl)-pyrid-2-
                        one
modified_base          22
                       mod_base = OTHER
                       note = N-ethylcytidine
SEQUENCE: 95
cttcttcctc ctcgtcatca tcat                                          24

SEQ ID NO: 96          moltype = DNA  length = 24
FEATURE                Location/Qualifiers
source                 1..24
```

-continued

```
                         mol_type = unassigned DNA
                         note = synthetic construct
                         organism = unidentified
modified_base            20
                         mod_base = OTHER
                         note = 2-aminopurine
modified_base            21
                         mod_base = OTHER
                         note =
                          3-(1-propynyl)-5-(1'-beta-D-2'-deoxyribofuranosyl)-pyrid-2-
                          one
SEQUENCE: 96
cttcttcctc ctcgtcatca tcat                                             24

SEQ ID NO: 97            moltype = DNA  length = 24
FEATURE                  Location/Qualifiers
source                   1..24
                         mol_type = unassigned DNA
                         note = synthetic construct
                         organism = unidentified
modified_base            20
                         mod_base = OTHER
                         note = 2-aminopurine
modified_base            22
                         mod_base = OTHER
                         note = N-ethylcytidine
SEQUENCE: 97
cttcttcctc ctcgtcatca tcat                                             24

SEQ ID NO: 98            moltype = DNA  length = 20
FEATURE                  Location/Qualifiers
source                   1..20
                         mol_type = unassigned DNA
                         note = synthetic construct
                         organism = unidentified
modified_base            17
                         mod_base = OTHER
                         note = inosine
modified_base            18
                         mod_base = OTHER
                         note = 2-aminopurine
SEQUENCE: 98
gaccccgata ggccatgatg                                                  20

SEQ ID NO: 99            moltype = DNA  length = 20
FEATURE                  Location/Qualifiers
source                   1..20
                         mol_type = unassigned DNA
                         note = synthetic construct
                         organism = unidentified
modified_base            18
                         mod_base = OTHER
                         note = 2-aminopurine
modified_base            19
                         mod_base = OTHER
                         note =
                          3-(1-propynyl)-5-(1'-beta-D-2'-deoxyribofuranosyl)-pyrid-2-
                          one
SEQUENCE: 99
gaccccgata ggccatgatg                                                  20

SEQ ID NO: 100           moltype = DNA  length = 20
FEATURE                  Location/Qualifiers
source                   1..20
                         mol_type = unassigned DNA
                         note = synthetic construct
                         organism = unidentified
modified_base            17
                         mod_base = OTHER
                         note = inosine
modified_base            19
                         mod_base = OTHER
                         note =
                          3-(1-propynyl)-5-(1'-beta-D-2'-deoxyribofuranosyl)-pyrid-2-
                          one
SEQUENCE: 100
gaccccgata ggccatgatg                                                  20

SEQ ID NO: 101           moltype = DNA  length = 20
```

-continued

```
FEATURE                Location/Qualifiers
source                 1..20
                       mol_type = unassigned DNA
                       note = synthetic construct
                       organism = unidentified
modified_base          16
                       mod_base = OTHER
                       note =
                        3-(1-propynyl)-5-(1'-beta-D-2'-deoxyribofuranosyl)-pyrid-2-
                        one
modified_base          19
                       mod_base = OTHER
                       note =
                        3-(1-propynyl)-5-(1'-beta-D-2'-deoxyribofuranosyl)-pyrid-2-
                        one
SEQUENCE: 101
gaccccgata ggccatgatg                                          20

SEQ ID NO: 102         moltype = DNA  length = 20
FEATURE                Location/Qualifiers
source                 1..20
                       mol_type = unassigned DNA
                       note = synthetic construct
                       organism = unidentified
modified_base          16
                       mod_base = OTHER
                       note =
                        3-(1-propynyl)-5-(1'-beta-D-2'-deoxyribofuranosyl)-pyrid-2-
                        one
modified_base          18
                       mod_base = OTHER
                       note = 2-aminopurine
SEQUENCE: 102
gaccccgata ggccatgatg                                          20

SEQ ID NO: 103         moltype = DNA  length = 28
FEATURE                Location/Qualifiers
source                 1..28
                       mol_type = unassigned DNA
                       note = synthetic construct
                       organism = unidentified
modified_base          27
                       mod_base = OTHER
                       note = inosine
SEQUENCE: 103
gtgattttga gaaatctttc ctttgagg                                 28

SEQ ID NO: 104         moltype = DNA  length = 28
FEATURE                Location/Qualifiers
source                 1..28
                       mol_type = unassigned DNA
                       note = synthetic construct
                       organism = unidentified
modified_base          26
                       mod_base = OTHER
                       note = 2-aminopurine
modified_base          27
                       mod_base = OTHER
                       note = inosine
SEQUENCE: 104
gtgattttga gaaatctttc ctttgagg                                 28

SEQ ID NO: 105         moltype = DNA  length = 20
FEATURE                Location/Qualifiers
source                 1..20
                       mol_type = unassigned DNA
                       note = synthetic construct
                       organism = unidentified
modified_base          18
                       mod_base = OTHER
                       note = N-ethylcytidine
SEQUENCE: 105
ggtacaggga gaggagcctc                                          20

SEQ ID NO: 106         moltype = DNA  length = 20
FEATURE                Location/Qualifiers
source                 1..20
                       mol_type = unassigned DNA
                       note = synthetic construct
```

-continued

```
                        organism = unidentified
modified_base           18
                        mod_base = OTHER
                        note = N-ethylcytidine
modified_base           19
                        mod_base = OTHER
                        note =
                         3-(1-propynyl)-5-(1'-beta-D-2'-deoxyribofuranosyl)-pyrid-2-
                         one
SEQUENCE: 106
ggtacaggga gaggagcctc                                                20

SEQ ID NO: 107          moltype = DNA  length = 20
FEATURE                 Location/Qualifiers
source                  1..20
                        mol_type = unassigned DNA
                        note = synthetic construct
                        organism = unidentified
modified_base           17
                        mod_base = OTHER
                        note = N-ethylcytidine
modified_base           19
                        mod_base = OTHER
                        note =
                         3-(1-propynyl)-5-(1'-beta-D-2'-deoxyribofuranosyl)-pyrid-2-
                         one
SEQUENCE: 107
ggtacaggga gaggagcctc                                                20

SEQ ID NO: 108          moltype = DNA  length = 31
FEATURE                 Location/Qualifiers
source                  1..31
                        mol_type = unassigned DNA
                        note = synthetic construct
                        organism = unidentified
modified_base           29
                        mod_base = OTHER
                        note = 2-aminopurine
SEQUENCE: 108
gccttaaaga aataaaatga ctatgtgcag a                                   31

SEQ ID NO: 109          moltype = DNA  length = 31
FEATURE                 Location/Qualifiers
source                  1..31
                        mol_type = unassigned DNA
                        note = synthetic construct
                        organism = unidentified
modified_base           30
                        mod_base = OTHER
                        note = inosine
SEQUENCE: 109
gccttaaaga aataaaatga ctatgtgcag a                                   31

SEQ ID NO: 110          moltype = DNA  length = 31
FEATURE                 Location/Qualifiers
source                  1..31
                        mol_type = unassigned DNA
                        note = synthetic construct
                        organism = unidentified
modified_base           29
                        mod_base = OTHER
                        note = 2-aminopurine
modified_base           30
                        mod_base = OTHER
                        note = inosine
SEQUENCE: 110
gccttaaaga aataaaatga ctatgtgcag a                                   31

SEQ ID NO: 111          moltype = DNA  length = 23
FEATURE                 Location/Qualifiers
source                  1..23
                        mol_type = unassigned DNA
                        note = synthetic construct
                        organism = unidentified
modified_base           22
                        mod_base = OTHER
                        note =
                         3-(1-propynyl)-5-(1'-beta-D-2'-deoxyribofuranosyl)-pyrid-2-
                         one
```

-continued

```
SEQUENCE: 111
gcttgaaact ccagcaaagt ctg                                          23

SEQ ID NO: 112          moltype = DNA  length = 23
FEATURE                 Location/Qualifiers
source                  1..23
                        mol_type = unassigned DNA
                        note = synthetic construct
                        organism = unidentified
modified_base           21
                        mod_base = OTHER
                        note = N-ethylcytidine
SEQUENCE: 112
gcttgaaact ccagcaaagt ctg                                          23

SEQ ID NO: 113          moltype = DNA  length = 23
FEATURE                 Location/Qualifiers
source                  1..23
                        mol_type = unassigned DNA
                        note = synthetic construct
                        organism = unidentified
modified_base           21
                        mod_base = OTHER
                        note = N-ethylcytidine
modified_base           22
                        mod_base = OTHER
                        note =
                         3-(1-propynyl)-5-(1'-beta-D-2'-deoxyribofuranosyl)-pyrid-2-
                         one
SEQUENCE: 113
gcttgaaact ccagcaaagt ctg                                          23

SEQ ID NO: 114          moltype = DNA  length = 23
FEATURE                 Location/Qualifiers
source                  1..23
                        mol_type = unassigned DNA
                        note = synthetic construct
                        organism = unidentified
modified_base           20
                        mod_base = OTHER
                        note =
                         3-(1-propynyl)-5-(1'-beta-D-2'-deoxyribofuranosyl)-pyrid-2-
                         one
modified_base           22
                        mod_base = OTHER
                        note =
                         3-(1-propynyl)-5-(1'-beta-D-2'-deoxyribofuranosyl)-pyrid-2-
                         one
SEQUENCE: 114
gcttgaaact ccagcaaagt ctg                                          23

SEQ ID NO: 115          moltype = DNA  length = 17
FEATURE                 Location/Qualifiers
source                  1..17
                        mol_type = unassigned DNA
                        note = synthetic construct
                        organism = unidentified
modified_base           14
                        mod_base = OTHER
                        note =
                         3-(1-propynyl)-5-(1'-beta-D-2'-deoxyribofuranosyl)-pyrid-2-
                         one
modified_base           16
                        mod_base = OTHER
                        note = N-ethylcytidine
SEQUENCE: 115
ccagatgcct ggctccg                                                 17

SEQ ID NO: 116          moltype = DNA  length = 20
FEATURE                 Location/Qualifiers
source                  1..20
                        mol_type = unassigned DNA
                        note = synthetic construct
                        organism = unidentified
modified_base           18
                        mod_base = OTHER
                        note = inosine
modified_base           19
                        mod_base = OTHER
```

```
                      note = 2-aminopurine
SEQUENCE: 116
gcctttgaag aggctcggag                                              20

SEQ ID NO: 117        moltype = DNA  length = 20
FEATURE               Location/Qualifiers
source                1..20
                      mol_type = unassigned DNA
                      note = synthetic construct
                      organism = unidentified
modified_base         17
                      mod_base = OTHER
                      note = Inosine
modified_base         19
                      mod_base = OTHER
                      note = 2-aminopurine
SEQUENCE: 117
gcctttgaag aggctcggag                                              20

SEQ ID NO: 118        moltype = DNA  length = 18
FEATURE               Location/Qualifiers
source                1..18
                      mol_type = unassigned DNA
                      note = synthetic construct
                      organism = unidentified
SEQUENCE: 118
cgacctggca gccaggaa                                                18

SEQ ID NO: 119        moltype = DNA  length = 19
FEATURE               Location/Qualifiers
source                1..19
                      mol_type = unassigned DNA
                      note = synthetic construct
                      organism = unidentified
SEQUENCE: 119
cctgctcctg ctcctcctc                                               19

SEQ ID NO: 120        moltype = DNA  length = 22
FEATURE               Location/Qualifiers
source                1..22
                      mol_type = unassigned DNA
                      note = synthetic construct
                      organism = unidentified
SEQUENCE: 120
tgcctccttc tgcatggtat tc                                           22

SEQ ID NO: 121        moltype = DNA  length = 21
FEATURE               Location/Qualifiers
source                1..21
                      mol_type = unassigned DNA
                      note = synthetic construct
                      organism = unidentified
SEQUENCE: 121
gccagtgcaa ccattatccg g                                            21

SEQ ID NO: 122        moltype = DNA  length = 17
FEATURE               Location/Qualifiers
source                1..17
                      mol_type = unassigned DNA
                      note = synthetic construct
                      organism = unidentified
SEQUENCE: 122
tgatgggggg ccatccc                                                 17

SEQ ID NO: 123        moltype = DNA  length = 19
FEATURE               Location/Qualifiers
source                1..19
                      mol_type = unassigned DNA
                      note = synthetic construct
                      organism = unidentified
SEQUENCE: 123
cccttctcca cctcttgcc                                               19

SEQ ID NO: 124        moltype = DNA  length = 20
FEATURE               Location/Qualifiers
source                1..20
                      mol_type = unassigned DNA
                      note = synthetic construct
                      organism = unidentified
```

-continued

```
SEQUENCE: 124
tcccagtgat agagcccagt                                              20

SEQ ID NO: 125          moltype = DNA  length = 19
FEATURE                 Location/Qualifiers
source                  1..19
                        mol_type = unassigned DNA
                        note = synthetic construct
                        organism = unidentified
SEQUENCE: 125
agacatggaa gaggcgagc                                               19

SEQ ID NO: 126          moltype = DNA  length = 15
FEATURE                 Location/Qualifiers
source                  1..15
                        mol_type = unassigned DNA
                        note = synthetic construct
                        organism = unidentified
SEQUENCE: 126
agccggacgt cgtgc                                                   15

SEQ ID NO: 127          moltype = DNA  length = 19
FEATURE                 Location/Qualifiers
source                  1..19
                        mol_type = unassigned DNA
                        note = synthetic construct
                        organism = unidentified
SEQUENCE: 127
cacggacgag gcaactttc                                               19

SEQ ID NO: 128          moltype = DNA  length = 17
FEATURE                 Location/Qualifiers
source                  1..17
                        mol_type = unassigned DNA
                        note = synthetic construct
                        organism = unidentified
SEQUENCE: 128
tgcctcggaa ccctcct                                                 17

SEQ ID NO: 129          moltype = DNA  length = 19
FEATURE                 Location/Qualifiers
source                  1..19
                        mol_type = unassigned DNA
                        note = synthetic construct
                        organism = unidentified
SEQUENCE: 129
cagggagagc tggtccttc                                               19

SEQ ID NO: 130          moltype = DNA  length = 17
FEATURE                 Location/Qualifiers
source                  1..17
                        mol_type = unassigned DNA
                        note = synthetic construct
                        organism = unidentified
SEQUENCE: 130
gcttgggcgg ggcctaa                                                 17

SEQ ID NO: 131          moltype = DNA  length = 29
FEATURE                 Location/Qualifiers
source                  1..29
                        mol_type = unassigned DNA
                        note = synthetic construct
                        organism = unidentified
SEQUENCE: 131
gggaaatgga ggataagaac attattcaa                                    29

SEQ ID NO: 132          moltype = DNA  length = 18
FEATURE                 Location/Qualifiers
source                  1..18
                        mol_type = unassigned DNA
                        note = synthetic construct
                        organism = unidentified
modified_base           16
                        mod_base = OTHER
                        note = inosine
modified_base           17
                        mod_base = OTHER
                        note = 2-aminopurine
SEQUENCE: 132
```

-continued

```
cgacctggca gccaggaa                                              18

SEQ ID NO: 133         moltype = DNA  length = 19
FEATURE                Location/Qualifiers
source                 1..19
                       mol_type = unassigned DNA
                       note = synthetic construct
                       organism = unidentified
modified_base          16
                       mod_base = OTHER
                       note = N-ethylcytidine
modified_base          17
                       mod_base = OTHER
                       note = N-ethylcytidine
SEQUENCE: 133
cctgctcctg ctcctcctc                                             19

SEQ ID NO: 134         moltype = DNA  length = 22
FEATURE                Location/Qualifiers
source                 1..22
                       mol_type = unassigned DNA
                       note = synthetic construct
                       organism = unidentified
modified_base          19
                       mod_base = OTHER
                       note = 2-aminopurine
modified_base          18
                       mod_base = OTHER
                       note =
                        3-(1-propynyl)-5-(1'-beta-D-2'-deoxyribofuranosyl)-pyrid-2-
                        one
SEQUENCE: 134
tgcctccttc tgcatggtat tc                                         22

SEQ ID NO: 135         moltype = DNA  length = 21
FEATURE                Location/Qualifiers
source                 1..21
                       mol_type = unassigned DNA
                       note = synthetic construct
                       organism = unidentified
modified_base          19
                       mod_base = OTHER
                       note = N-ethylcytidine
modified_base          20
                       mod_base = OTHER
                       note = inosine
SEQUENCE: 135
gccagtgcaa ccattatccg g                                          21

SEQ ID NO: 136         moltype = DNA  length = 17
FEATURE                Location/Qualifiers
source                 1..17
                       mol_type = unassigned DNA
                       note = synthetic construct
                       organism = unidentified
modified_base          16
                       mod_base = OTHER
                       note = N-ethylcytidine
SEQUENCE: 136
tgatgggggg ccatccc                                               17

SEQ ID NO: 137         moltype = DNA  length = 19
FEATURE                Location/Qualifiers
source                 1..19
                       mol_type = unassigned DNA
                       note = synthetic construct
                       organism = unidentified
modified_base          18
                       mod_base = OTHER
                       note = N-ethylcytidine
modified_base          16
                       mod_base = OTHER
                       note =
                        3-(1-propynyl)-5-(1'-beta-D-2'-deoxyribofuranosyl)-pyrid-2-
                        one
SEQUENCE: 137
cccttctcca cctcttgcc                                             19

SEQ ID NO: 138         moltype = DNA  length = 20
```

-continued

```
FEATURE                Location/Qualifiers
source                 1..20
                       mol_type = unassigned DNA
                       note = synthetic construct
                       organism = unidentified
modified_base          18
                       mod_base = OTHER
                       note = 2-aminopurine
SEQUENCE: 138
tcccagtgat agagcccagt                                          20

SEQ ID NO: 139         moltype = DNA  length = 19
FEATURE                Location/Qualifiers
source                 1..19
                       mol_type = unassigned DNA
                       note = synthetic construct
                       organism = unidentified
modified_base          17
                       mod_base = OTHER
                       note = 2-aminopurine
modified_base          18
                       mod_base = OTHER
                       note = inosine
SEQUENCE: 139
agacatggaa gaggcgagc                                           19

SEQ ID NO: 140         moltype = DNA  length = 15
FEATURE                Location/Qualifiers
source                 1..15
                       mol_type = unassigned DNA
                       note = synthetic construct
                       organism = unidentified
modified_base          14
                       mod_base = OTHER
                       note = inosine
SEQUENCE: 140
agccggacgt cgtgc                                               15

SEQ ID NO: 141         moltype = DNA  length = 19
FEATURE                Location/Qualifiers
source                 1..19
                       mol_type = unassigned DNA
                       note = synthetic construct
                       organism = unidentified
modified_base          15
                       mod_base = OTHER
                       note = N-ethylcytidine
modified_base          17
                       mod_base = OTHER
                       note =
                        3-(1-propynyl)-5-(1'-beta-D-2'-deoxyribofuranosyl)-pyrid-2-
                        one
SEQUENCE: 141
cacggacgag gcaactttc                                           19

SEQ ID NO: 142         moltype = DNA  length = 17
FEATURE                Location/Qualifiers
source                 1..17
                       mol_type = unassigned DNA
                       note = synthetic construct
                       organism = unidentified
modified_base          15
                       mod_base = OTHER
                       note = N-ethylcytidine
SEQUENCE: 142
tgcctcggaa ccctcct                                             17

SEQ ID NO: 143         moltype = DNA  length = 19
FEATURE                Location/Qualifiers
source                 1..19
                       mol_type = unassigned DNA
                       note = synthetic construct
                       organism = unidentified
modified_base          16
                       mod_base = OTHER
                       note = N-ethylcytidine
SEQUENCE: 143
cagggagagc tggtccttc                                           19
```

-continued

```
SEQ ID NO: 144          moltype = DNA  length = 17
FEATURE                 Location/Qualifiers
source                  1..17
                        mol_type = unassigned DNA
                        note = synthetic construct
                        organism = unidentified
modified_base           12
                        mod_base = OTHER
                        note = inosine
modified_base           14
                        mod_base = OTHER
                        note = N-ethylcytidine
SEQUENCE: 144
gcttgggcgg ggcctaa                                          17

SEQ ID NO: 145          moltype = DNA  length = 29
FEATURE                 Location/Qualifiers
source                  1..29
                        mol_type = unassigned DNA
                        note = synthetic construct
                        organism = unidentified
modified_base           27
                        mod_base = OTHER
                        note = N-ethylcytidine
modified_base           26
                        mod_base = OTHER
                        note =
                         3-(1-propynyl)-5-(1'-beta-D-2'-deoxyribofuranosyl)-pyrid-2-
                         one
SEQUENCE: 145
gggaaatgga ggataagaac attattcaa                             29
```

NUCLEOTIDE ANALOGS FOR EFFICIENT DNA AND RNA AMPLIFICATION

STATEMENT REGARDING FEDERALLY SPONSORED RESEARCH OR DEVELOPMENT

This invention was made with government support under grants from the National Institutes of Health (1R01AI135146-01A1). The government has certain rights in the invention.

CROSS REFERENCE TO RELATED APPLICATIONS

Not applicable.

THE NAMES OF THE PARTIES TO A JOINT RESEARCH AGREEMENT

Not applicable

INCORPORATION-BY-REFERENCE OF MATERIAL SUBMITTED

An XML file for a "Sequence Listing XML" submitted via the USPTO patent electronic filing with the name ("MODURA_SeqListing"), the date of creation (14 Apr. 2025), and the file size (214,614 bytes).

FIELD OF THE INVENTION

This invention relates to DNA and RNA nucleoside and nucleotide analogs, and to oligonucleotide analogs that incorporate these nucleoside and nucleotide analogs. More specifically, it relates to oligonucleotide analogs having preselected sequences, wherein one or more of their constituent standard nucleotides is replaced by one or more of the nucleotide analogs of the instant invention. This invention further relates to mixtures of such oligonucleotide analogs, where individual oligonucleotide analogs in said mixtures have reduced interactions with other oligonucleotide analogs in said mixtures, but productively interact with standard oligonucleotides (e.g. DNA and RNA targets) in said mixtures.

BACKGROUND OF THE INVENTION

The art recognizes the utility of short (10-40 nucleotides) canonical (or standard) oligonucleotides" assembled from (for example) adenosine, guanosine, cytidine, and thymidine, that are substantially complementary to longer target oligonucleotides, to which they anneal, or hybridize, at a preselected temperature in water having preselected cosolutes (e.g. buffers or salts). Here, "substantially complementary" means that at least 7 out of 8 nucleotides in substantially complementary strands match each other according to Watson-Crick-Franklin (WCF) pairing rules. This allows, for example, hybridization of canonical oligonucleotide primers to "target oligonucleotides" following well-known WCF base pairs during steps in the polymerase chain reaction (PCR)[1].

The art also recognizes utility of analogs of those short canonical oligonucleotides where individual nucleotides are replaced by nucleotide analogs. As a consequence of those replacements, derived oligonucleotides no longer hybridize productively to other derived oligonucleotides, but still productively hybridize to complementary canonical target oligonucleotides that lack the replacements. The derived oligonucleotides have been called "self-avoiding" in the art.[2] Self-avoiding oligonucleotides are especially valuable when attempting to amplify a segment of a long target oligonucleotide (including DNA and RNA targets), where one of the oligonucleotides acts as a "forward primer", and the other acts as a "reverse primer", by binding to that "target".

In such amplifications, the single stranded canonical priming oligonucleotides are present in (often large) excess over the target. Therefore, these priming oligonucleotides encounter and interact with other priming oligonucleotides, often (much) more frequently than they encounter and interact with the target oligonucleotide. When two primers interact with each other, one can serve as a template for polymerase-catalyzed extension of the other. In PCR, common outcomes of this undesired interaction are "primer dimers".[3] Among other disadvantages, primer dimers consume amplification resources unproductively. Other off-target hybridization to "background" DNA also present in many biological samples create off-target amplicons that can, inter alia, consume amplification resources unproductively, and confuse signal readout.

Self-avoiding primers are especially important in amplifications that operate at lower temperatures, for example, in recombinase-polymerase amplifications[4] and helicase-dependent amplifications.[5] However, primer dimers also are obstacles in polymerase chain reaction (PCR) amplifications that involve thermal cycling, and especially so in multiplexed PCR.[6] As the number of primer oligonucleotides increases, with two added primers generally required for each added target, the number of possible primer-primer interactions scales approximately with the square of the number of targets. Primer-primer interactions therefore effectively prevent PCR mixtures from amplifying more than ~20 different targets. Even the best computer designs cannot prevent primer-primer interactions from defeating multiplexed PCR with 20 or more targets.[7]

Self-avoiding primers are disclosed in the art, such as U.S. Pat. No. 9,249,458.[8] That art teaches that "self-avoidance" can be obtained by substituting G, A, C, T with "self-avoiding" nucleotide analogs, designated in that art as G*, A*, C* and T*. Here, G*:C, C*:G, A*:T, and T*:A pairs contribute to the overall stability of a duplex. However, A*:T* and G*:C* pairs significantly reduce the overall stability of a duplex relative to analogous duplexes with only standard oligonucleotides. Thus, oligonucleotides containing G*, A*, C*, and T* do not bind to (they "avoid") other oligonucleotides containing G*, A*, C*, and T*.

Choice of the heterocycles to implement the self-avoiding concept has undergone development. Thus, early art teaches that inosine (the heterocycle is hypoxanthine) might serve as a self-avoiding replacement for guanosine (the heterocycle is guanine), and zebularine (the heterocycle is pyrimidin-2-one) might serve as a "self-avoiding" replacement for cytidine. Here, inosine:cytidine pairs are taught to contribute to the stability of a duplex where there are paired, and zebularine:guanosine pairs contribute to the stability of a duplex where there are paired. However, inosine:zebularine pairs are taught to not contribute to the stability of a duplex where there are paired.[2]

Unfortunately, the pyrimidin-2-one heterocycle in zebularine is chemically unstable with respect to chemical transformation under both acidic and basic conditions. This makes it difficult to synthesize oligonucleotides that contain zebularine. Thus, in the art, N-methylcytidine, N-ethylcytidine, 5-methyl-N-methylcytidine, and/or 5-methyl-N-ethylcytidine have been taught to be self-avoiding replacements for cytidine [U.S. Pat. No. 9,249,458]. These form a pair with guanosine that is weaker than the C:G pair. However, the N-ethylcytidine:inosine pair does not contribute to duplex stability enough to compensate for the loss of water solvation when the pair is formed. This makes the pair "self-avoiding".

Likewise, the same art teaches that 2-aminopurine and 2,6-diaminopurine nucleosides can have utility as A*, with 2-thiothymidine being the corresponding T*. The 5-methyl-3-pyridin-2-one nucleoside that might serve as a T* is taught to be unsatisfactory in the literature by McLaughlin and his coworkers.[9,10] These authors reported that for a reference self-pairing 12-mer, under a defined set of conditions, the melting temperature drops to from 67° C. to 56° C. when 5-methyl-3-pyridin-2-ones replaced two thymines in two central A:T pairs. Likewise, they reported that the melting temperature drops to 62° C. when a single 5-methyl-3-pyridin-2-one replaces a thymine. These large drops meant that stable duplexes failed to form when they paired standard A with 5-methyl-3-pyridin-2-one nucleoside.

BRIEF SUMMARY OF THE INVENTION

The instant invention is based on the discovery that 3-(alkynyl)-5-(1'-beta-D-2'-deoxyribofuranosyl)-pyrid-2-one and 3-(alkenyl)-5-(1'-beta-D-2'-deoxyribofuranosyl)-pyrid-2-one nucleosides are excellent self-avoiding T* replacements for thymidine. To systematize the nomenclature in this presentation, 3-(1-propynyl)-5-(1'-beta-D-2'-deoxyribofuranosyl)-pyrid-2-one, a presently preferred self-avoiding T*, is designed by a lower case bold italicized t. 2-Aminopurine nucleoside, a presently preferred self-avoiding A*, is designated by a lower case bold italicized a. Inosine, a presently preferred self-avoiding G*, is designated by a lower case bold italicized g. N-ethylcytosine, a presently preferred self-avoiding C*, is designated by a lower case bold italicized c. These lower case bold italics letters also refer to the heterocycles on the nucleoside, as context makes clear.

As another discovery, t:A pairs proved to contribute similarly to duplex stability as the a:T, g:C and c:G pairs. These are called "Mutually Orthogonal DNA with Uniformly Reliable Affinities" (MODURA). This observation supports these utilities:

(A) oligonucleotide analogs where, in their pre-selected sequences, selected thymidines are replaced by ts to cause them to be self-avoiding.

(B) processes that use such oligonucleotide analogs primers in amplifications, including isothermal and PCR amplifications, and in multiplexed amplifications, including multiplexed PCR assays, where the primers are self-avoiding.

(C) oligonucleotide analogs where, in a pre-selected sequence, in addition to one or more thymidines being replaced by t (or another T* as disclosed here for the first time), one or more of the guanines are independently replaced by hypoxanthine as g, or more of the adenines are independently replaced by 2,6-diaminopurine or 2-aminopurine as a, and/or one or more of the cytosines are independently replaced by N-methylcytidine or N-ethylcytidine as c.

(D) processes that use the oligonucleotide analogs in Invention (C) as primers in amplifications, including isothermal amplifications and PCR amplifications, and in multiplexed amplifications, including multiplexed PCR amplifications.

(E) collections of oligonucleotide analogs that (i) show low interaction with each other, with (ii) comparable affinity to canonical complementary oligonucleotides. These have utility, inter alia, in multiplexed PCR, where the presently preferred combinations include at least 8 MODURA oligonucleotides.

BRIEF DESCRIPTION OF THE SEVERAL VIEWS OF THE DRAWINGS

FIG. 7-1. Formation of useless primer dimers versus useful amplicons with or without a or t modification (Example 5). The melting temperature profiles, monitored with intercalated EvaGreen® dye in Example 5, show primer dimer and PCR amplicon formation with standard primers having 5 nt overlap at their 3' ends and t, g, a, and c-modifications in the 5 nt overlap region (Table 4-2). In Table 4-2, primer sequences are denoted as fragments, specifically the 5 nt overlap at their 3' ends. Standard primers with perfect 5 nt overlap at their 3' ends: Set A (T:A, SEQ ID NO: 77+SEQ ID NO: 79) produce predominantly primer dimer and essentially no amplicon. Primer with t modification: Set B (t:A, SEQ ID NO: 89+SEQ ID NO: 79) prevents primer dimer formation and produce only PCR amplicon. Primer with a modification: Set C (T:a, SEQ ID NO: 77+SEQ ID NO: 91) generates both primer dimer and PCR amplicon. Primers with t and a modifications: Set D (t:a, SEQ ID NO: 89+SEQ ID NO: 91) produce only PCR amplicon. Both Set B and Set D indicate that t is highly effective at avoiding primer dimer. These are unexpected results.

FIG. 7-2. Formation of useless primer dimers versus useful amplicons with or without g or c modifications (Example 6). The melting profiles, monitored with intercalated EvaGreen® dye in Example 6, show primer dimer and PCR amplicon formation with standard primers having 5 nt overlap at their 3' ends and t, g, a, and c-modifications in the 5 nt overlap region (Table 4-2). In Table 4-2, Standard primers with perfect 5 nt overlap at their 3' ends: Set A (C:G, SEQ ID NO: 77+SEQ ID NO: 79) produce predominantly primer dimer and essentially no amplicon. Primer with c modification: Set E (c:G, SEQ ID NO: 90+SEQ ID NO: 79) generates both primer dimer and PCR amplicon. Primer with g modifications (Set F (C:g, SEQ ID NO: 77+SEQ ID NO: 92) give primer dimer and amplicons. Primers with c and g modifications (Set G (c:g, SEQ ID NO: 90+SEQ ID NO: 92)) produce only PCR amplicon. These results indicate that both c and g are required to completely avoiding primer dimers and t is the most effective component to prevent primer dimers (FIG. 7-1 and FIG. 7-2).

DETAILED DESCRIPTION OF THE INVENTION

Here, an "oligonucleotide" is a DNA or RNA molecule comprising standard canonical nucleotide "building blocks". That oligonucleotide can have non-nucleoside components attached to its 5'- or 3'-ends, made by methods known in the art. Further, the canonical nucleotides can themselves carry tags or appendages, as well known in the art.

Whenever any of the nucleotides in an oligonucleotide have nucleotide analogs of the instant invention, specifically, 3-alkenyl or 3-alkynyl-3-pyridin-2-one nucleotides, where the pyridone heterocycle is attached to the sugar ring at its 5-position, an N-methyl or N-ethylcytosine nucleotide, a 2-aminopurine or diaminopurine nucleotide, and/or a hyoxanthine nucleotide, the molecule is referred to as an "oligonucleotide analog". It should be noted that in the art, a hypoxanthine nucleoside is also called inosine, while a diaminopurine nucleotide is often called aminoadenosine.

At points in this description, an oligonucleotide sequence build from canonical nucleotides is pre-selected, or designed. Then, one or more of the standard nucleotides is said to be "replaced" by nucleotide analogs of the instant invention. This is understood to be a replacement in the design, not a chemical process by which canonical oligonucleotides are chemically transformed.

Figure 1:
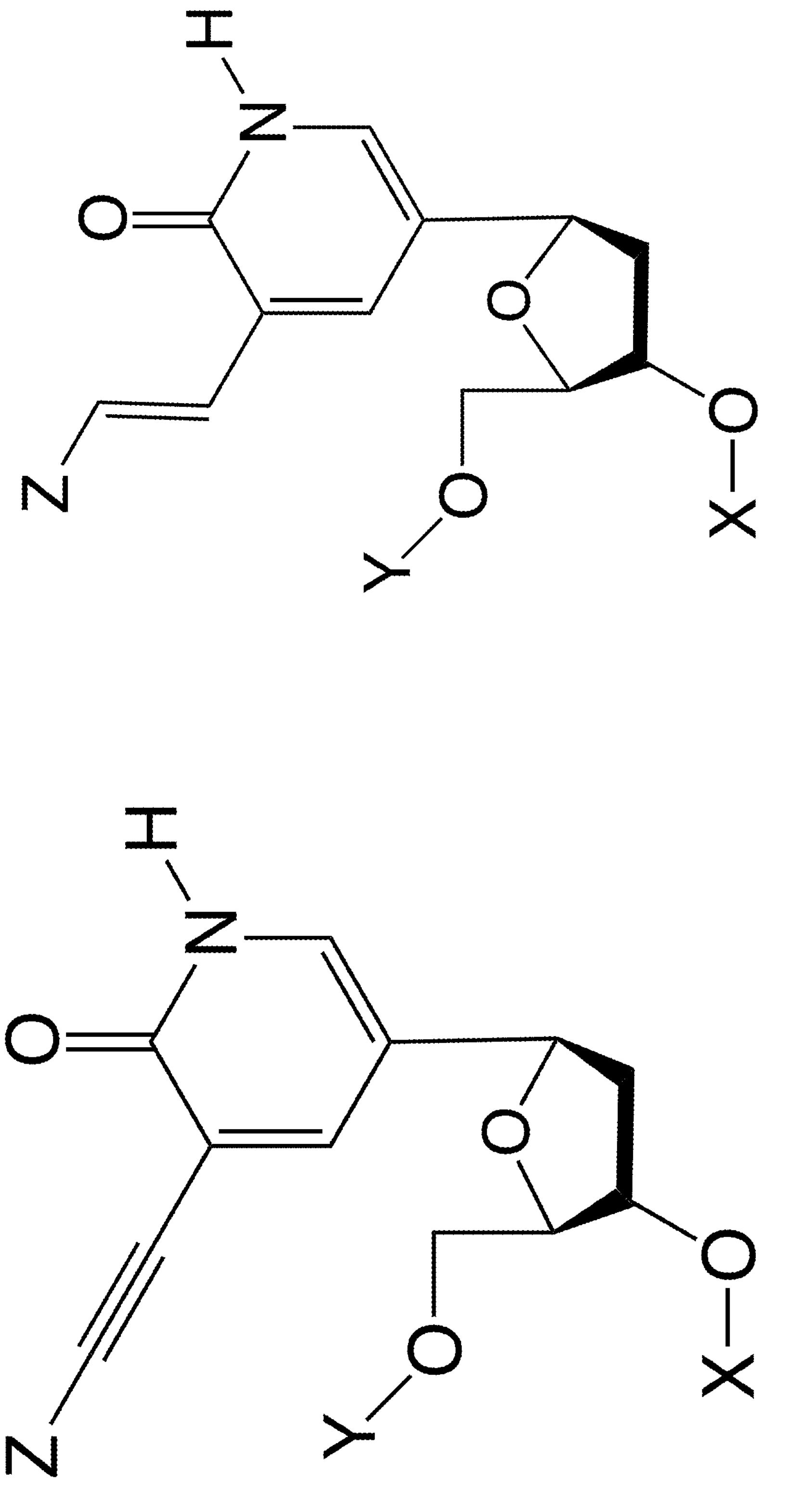
FIG. 1. Chemical structure of the nucleoside analogs of the instant invention. Here, a standard nucleobase is replaced by a substituted pyridone heterocycle. Z is preferred to be —H and —$CH_3$, but may also be a longer alkyl group, including an alkyl group carrying a tag, such as a fluorescent tag or biotin. The X and Y substituents depend on context. Thus, in the nucleoside form, X and Y are both —H. When incorporated into a DNA molecule at the 5'-end, Y is —H and X is a —$PO_2$—O-DNA molecule. When incorporated into a DNA molecule at the 3'-end, X is —H and Y is a —$PO_2$—O-DNA segments. When incorporated into the middle of a DNA segments, X and Y are both —$PO_2$—O-DNA segments. The —Y group can also be a diphosphate or triphosphate group. For solid phase oligonucleotide synthesis, Y is a protecting group, such as dimethoxytrityl, and X is a phosphoramidite group. For synthesis in the 5'-to-3' direction, the protecting group and the phosphoramidite groups are reversed.

Several attempts made to synthesize alkynyl-3-pyridin-2-one nucleosides failed. These are summarized in FIG. 3 and Example 1. After these failures, further efforts obtained a procedure to synthesize 5-alkynyl-3-pyridin-2-one nucleosides, where the alkynyl unit was either ethynyl or 1-propynyl (FIG. 1).

Figure 4:
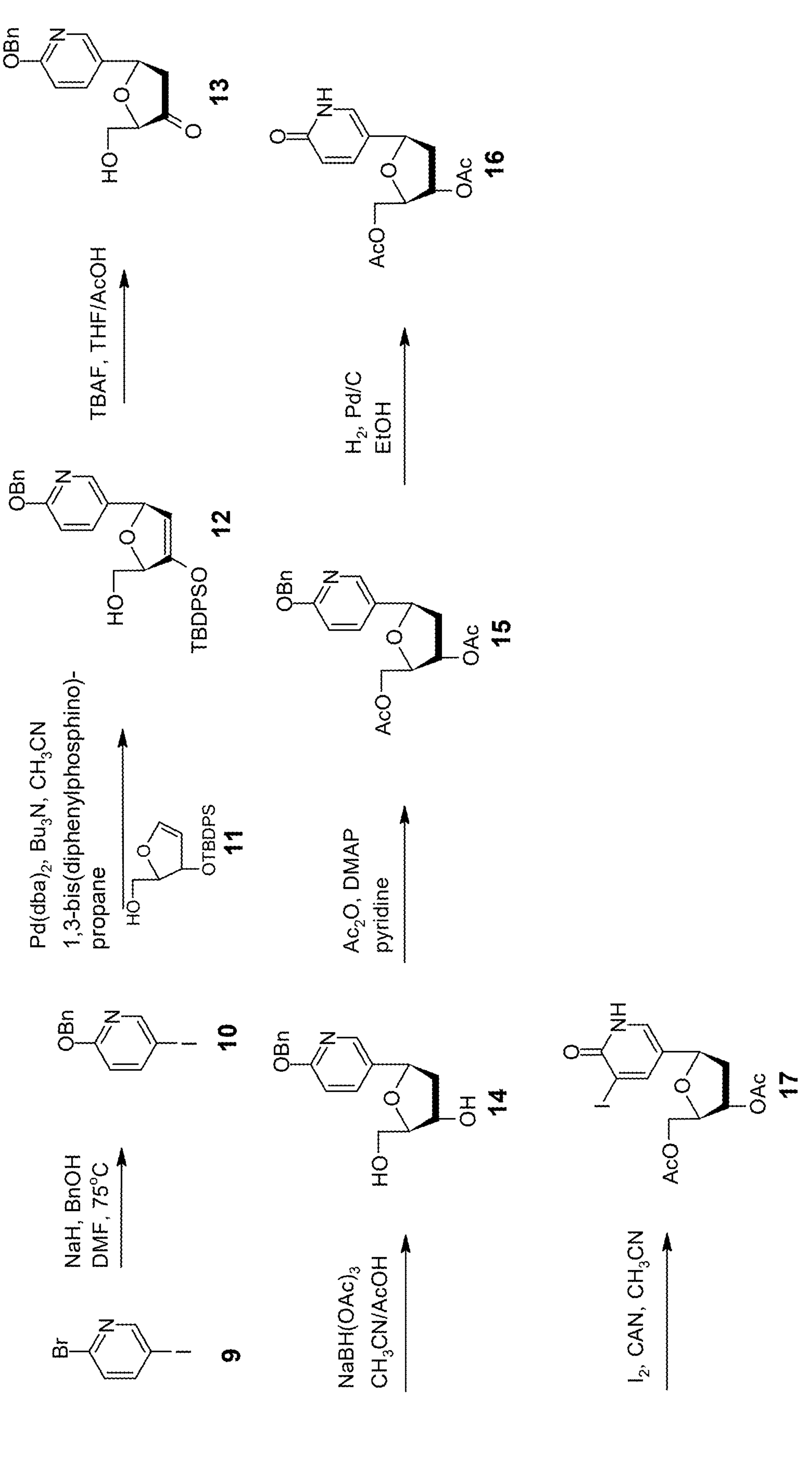
FIG. 4. Successful procedure to make the protected 5-iodo-3-pyridin-2-one nucleoside (Example 2).
Figure 5:
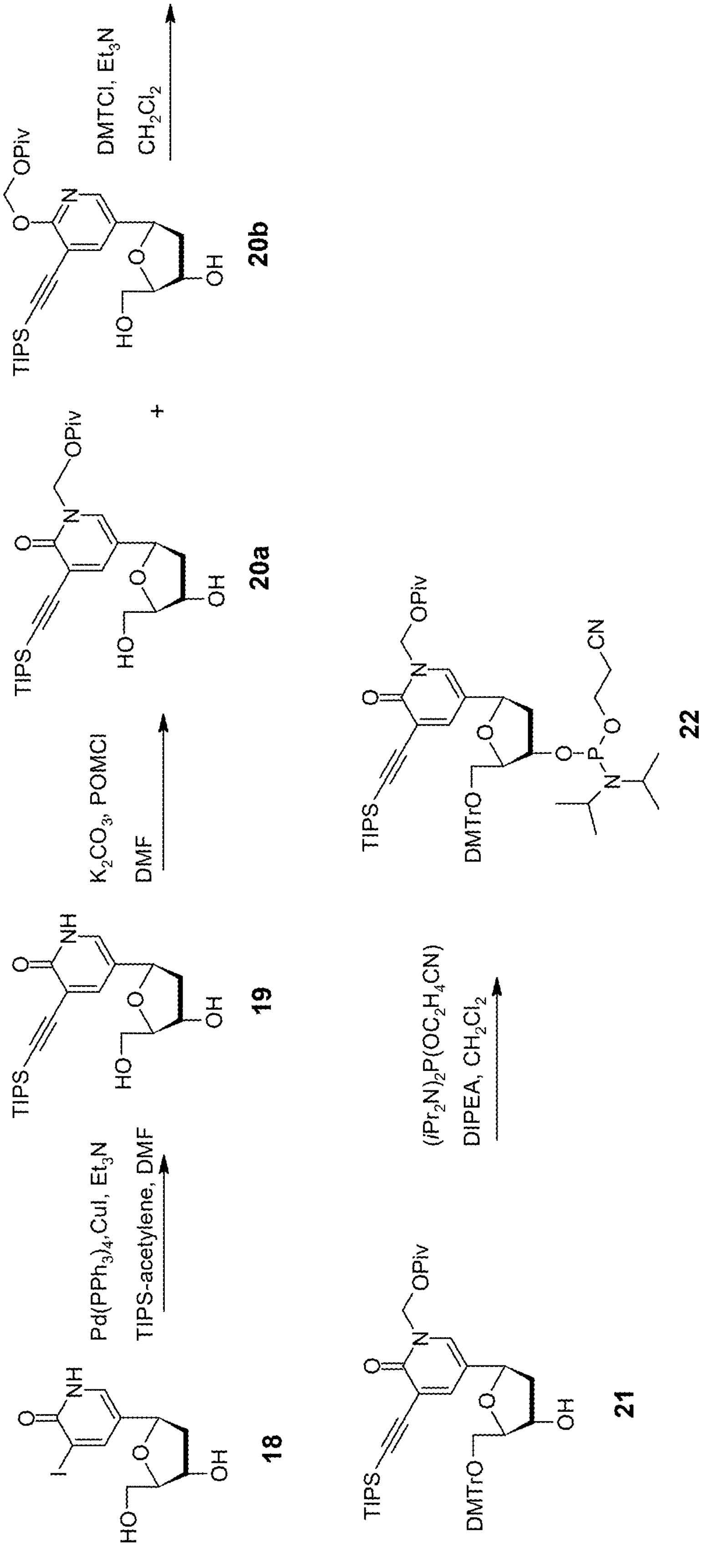
FIG. 5. Synthesis of protected phosphoramidite of the ethynyl version (Example 3), where the Z is H in the left structure of FIG. 1. Here, the —Z in FIG. 1 is —H.
Figure 6:
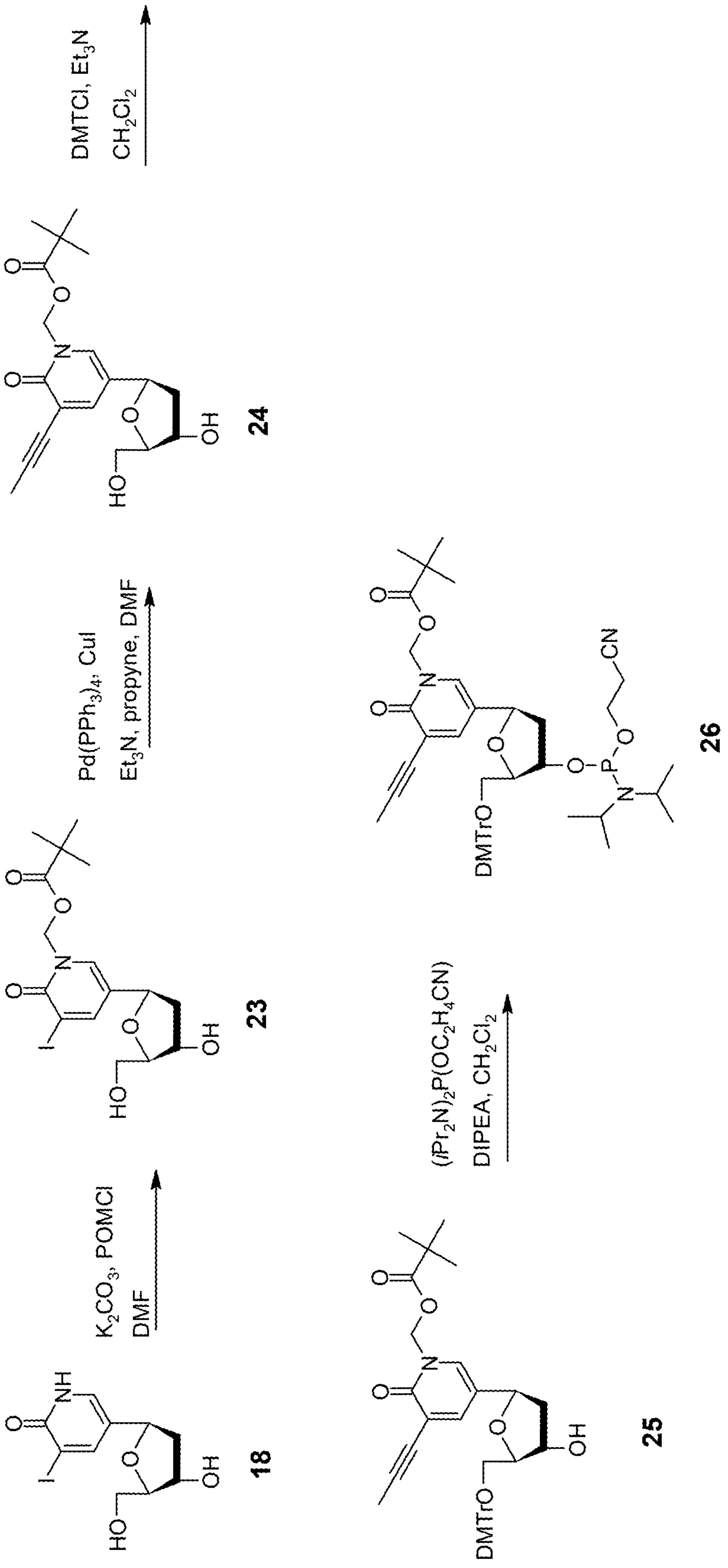
FIG. 6. Synthesis of 3-(1-propynyl)-5-(1'-beta-D-2'-deoxyribofuranosyl)-pyrid-2-one phosphoramidite (Example 4). Here, the —Z in FIG. 1 is —$CH_3$.
Figure 10:
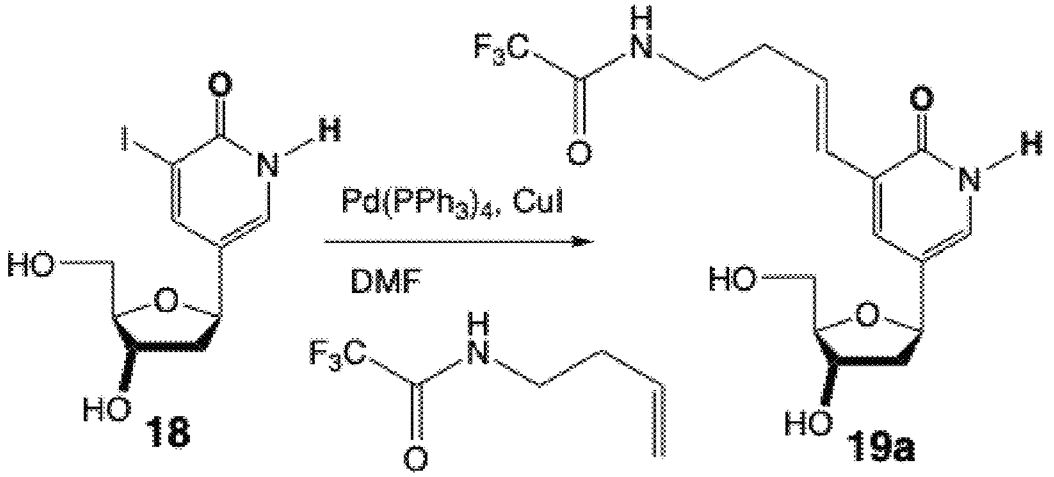
FIG. 10. Synthesis of a representative nucleoside with a 5-alkenyl and alkynyl substituents with tags.
Figure 10:
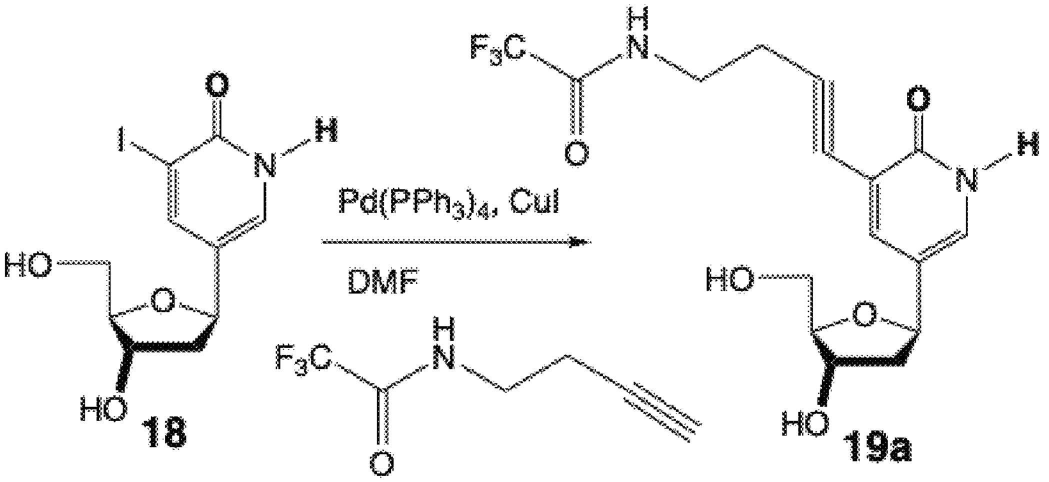

For all of these, a common 3-iodo-5-(2'-deoxyribosyl)-pyridin-2-one was prepared, as described in Example 2 (FIG. 4). The specific procedure to prepare the ethynyl derivative of this compound is given in Example 3 (FIG. 5). The specific procedure to prepare the 1-propynyl derivative of this compound is given in Example 4 (FIG. 6). Analogous approaches are expected to work for the corresponding alkenyl derivatives (FIG. 10).

These derivatives were then converted to protected phosphoramidites, which were used by standard solid phase phosphoramidite synthesis procedures (MerMade oligonucleotide synthesizer) to make a variety of oligonucleotides of preselected sequence where selected T, G, A, and C nucleotides are replaced by t, g, a, and c, respectively (Table 1). Table 2 reports melting temperature studies that show the midpoint of a thermal denaturation curve of WCF complementary oligonucleotides. Oligonucleotides containing 2-thiothymidine, taught in the literature as a self-avoiding thymidine analog, were also synthesized and their melting temperatures compared to those obtained with t (Table 1 and Table 2). Oligonucleotides were synthesized to contain one or two ts and one or more of the self-avoiding nucleotides inosine, N-ethylcytidine, and 2'-aminopurine nucleotide and these oligonucleotides were tested in PCR (Table 3, Table 4, Table 5 and Table 6).

While the data speak for themselves, these experiments discovered that t met all the requirements for a self-avoiding replacement for standard thymidine. The t:A base pair contributed to duplex stability similarly to the g:C, c:G, and a:T pairs, with modest dependence on sequence context. The contribution of the t:a pair to duplex stability was far less, as useful, indeed, substantially less than the contribution made by the c:g pair.

Oligonucleotides containing one t in sequences selected to bind to segments of target oligonucleotides (DNA and/or RNA) can serve as primers and support PCR amplifications. This was also the case for oligonucleotides having sequences selected to bind to segments of target oligonucleotides (DNA and/or RNA) that contained one or more ts and one or more self-avoiding nucleotides inosine, N-ethylcytidine, and 2'-aminopurine nucleotide.

As is known in the art, PCR targeted against one to six targets is frequently successful, even without using modified primers, provided that the primers are carefully designed. However, as disclosed in U.S. patent application Ser. No. 17/101,467, currently pending, even in low multiplexes, primer-primer interactions can defeat utility. This occurred in 2020 with the standard CDC primers that targeted the COVID-19 viral genome containing eight priming oligonucleotides, in a 4-fold multiplex. Primer-primer interactions rendered this 4-plex multiplex essentially useless. However, when the primers having the same sequences with G*, A*, C*, and T* (as 2-thiothymidine) replacements, a successful COVID-19 multiplex was created. Further applications are disclosed in 2-thiothymidine t, g, a, and c-containing primer sequences are given in U.S. patent application Ser. Nos. 18/528,230, 18/669,139, and 17/341,605, which are also incorporated herein by reference in its entirety.

The preferred melting temperature depends on the nature of the amplification architecture. For example, in PCR, where the duplexes are melted typically at temperatures above 85° C., the primers must anneal to the targets as the temperature is lowered and must remain annealed at the temperature at which primer extension occurs. Here, the preferred melting temperature of the primer-template complex is between 37° C. and 80° C. Temperatures in the higher range are often used when faster temperature cycling is used. However, in standard PCR, primer annealing and extension is done at 45° C. to 75° C., meaning that preferred PCR primers anneal to targets with melting temperatures preferably between 50° C. and 72° C. As is known in the art, the primer is lengthened at its 5'-end to obtain the melting temperatures taught herein. Primers containing g, a, c, and t replacements have a modestly lower melting temperature when bound to their complementary DNA or RNA sequences than standard primers without those modifications.

Isothermal amplifications use lower temperatures than PCR, and the preferred length of the primer depends on the amplification architecture. For example, in recombinase polymerase amplification (RPA), primer lengths are typically 30-40 nucleotides, corresponding to the recognition footprint of the recombinase. Loop amplification (LAMP), helicase-dependent amplification (HDA), and other isothermal amplification architectures are run at 37° C. to 70° C., preferred melting temperatures are dependent on the isothermal architecture. Strand displacement amplification (SDA) is likewise run at 37° C. or 65° C., the latter when a Bst polymerases (e.g. Bst 2.0 or 3.0, including their "warm start" variants) are used.

The length of the primer at its 5'-end is not specified in the instant invention. However, it must be substantially WCF complementary to its target. Its total sequence is preselected following WCF rules. The artisan may use standard computer software to predict the melting temperature of the full primers when hybridized to its target.

The MODURA t, g, a, and c-containing nucleotide analogs may be used in oligonucleotides that also include components of an artificially expanded genetic information system (AEGIS)[12], well known in the art, including in the parent applications of this application. These are analogs of nucleic acid that contain additional nucleotide pairs that recognize each other by an extended set of Watson-Crick complementarity rules. In standard DNA, A:T and G:C pairs follow two rules of complementarity: (a) size complementarity, where big purines pair with small pyrimidines, and (b) hydrogen bond complementarity, where hydrogen bond donors pair with hydrogen bond acceptors. The added AEGIS nucleotides still follow these two rules, but with rearranged hydrogen bond donors/acceptors. 12 building blocks forming 6 orthogonal pairs are possible in AEGIS. The added eight nucleotide analogues forming four orthogonal pairs can complement nothing in natural biology, and therefore are highly orthogonal tags for tagged PCR[13].

AEGIS-containing tags can be added to the 5'-ends of the primers containing the MODURA t, g, a, and c replacements.[6]

The oligonucleotides are synthesized by standard solid phase synthesis, well known in the art, preferably with standard protecting groups and using controlled pore glass as a support. The MODURA oligonucleotides are generally purified by HPLC, although standard desalting procedures well known in the art also work.

Self-avoiding primers, including 2-pyridone t, also improve the performance of random primers. This is, of course, done frequently in the art with 6 up to 10 nucleotides long random primers. Introduction of t, g, a, and c analogs into such random primers is another application of the inventions disclosed herein. Because addition of the analogs diminishes primer dimers relative to the fully standard DNA primers, the presently preferred length of random primers containing the analogs is from 6 to 10.

An important utility of multiplexed target amplification is as a first step in target detection. For example, in "all diseases in one sample" (ADIOS™) amplification, the capacity to identify each one of the pathogen from dozens of possible pathogens that might be present is required. Here, as before, multiple amplifications of all targets are not necessary, but the capacity to amplify any of the targets that might be present.

Thus, a process for copying a preselected target is taught in this specification as the elementary step. Here, extension of a DNA molecule via template-directed enzyme-catalyzed polymerization, where the target analyte is the template for that polymerization. Here, the process comprises contacting a rules-designed oligonucleotide in a mixture with a sample comprising that analyte. As is known in the art, that mixture must also comprise one or more polymerases, nucleoside triphosphates, and other components required for the polymerization to work, including salts and buffers. Downstream detection can be done by any of a number of methods in the art, including probing (e.g. TaqMan probe, molecular beacon), array-based hybridization, and sequencing, such as "next generation" sequencing or nanopore sequencing. These may also be an RNA polymerase, or a reverse transcriptase, the second having utility when the target molecules that serve as templates for a primer extension reaction are RNA molecules.

Examples 1-4 report efforts, failed and successful, to chemically synthesize 2-pyridone nucleoside t in forms suited for solid phase oligonucleotide synthesis. Table 1 and Table 2 report experiments to document the results that the t supports duplex formation with standard DNA. Examples 5-8 document the ability of oligonucleotides containing t, a, c, and g served as primers to support PCR (Table 4 and Table 5) and multiplexed PCR in Table 6).

As a summary of the experimental work that established the surprising results that demonstrate the utility of t, melting studies show that oligonucleotides containing 3-propynyl-2-pyridone nucleoside t have a desirably slightly lower $T_m$ when paired with adenosine (t:A) than those that pair the canonical thymidine and adenosine nucleosides (T:A). This is desirable because the same slightly lower $T_m$s are seen with other MODURA:standard pairs (Table 2). This allows ready design of useful sets of MODURA primers. Further, duplexes containing mispairs of t with G, C, and T have still lower $T_m$s (Table 2-2). 3-Propynyl-2-pyridone nucleoside t displays a self-avoiding property with 2-aminopurine a. Specifically, duplexes containing a t:a pair have a 6.9° C. average lower $T_m$ than reference duplexes containing standard T:A pairs (Table 2-4).

These melting studies show that t prevents primer dimer formation in enzyme-based PCR, when a is present in other oligonucleotides, to a useful extent. Studies with canonical nucleotides with perfect 3'-matches with 4 nucleotide and 5 nucleotide pairs show extensive primer dimer formation. Adding t creates analogous primers where PCR primer dimer formation is delayed ~1000-fold (Table 3-1 and 3-2). This outcome corresponds to data obtained from melting studies, where PCR artifact formation correlates with $T_m$ values observed with t:a and t:A pairs, especially when compared to melting temperatures are obtained with 2-thio-thymidine, as reported in the art.

Figure 2:
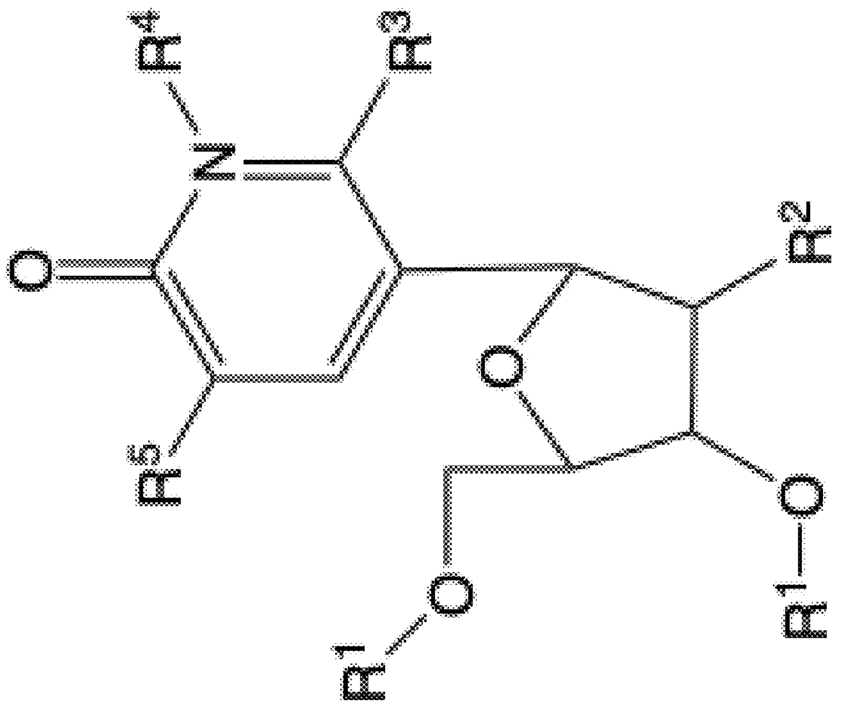
FIG. 2. Structure from the claims of U.S. Pat. No. 6,447,998[11]. Note the pentavalent carbon atoms. For the definitions of the R-groups, see the patent.
Figures 1, 7:
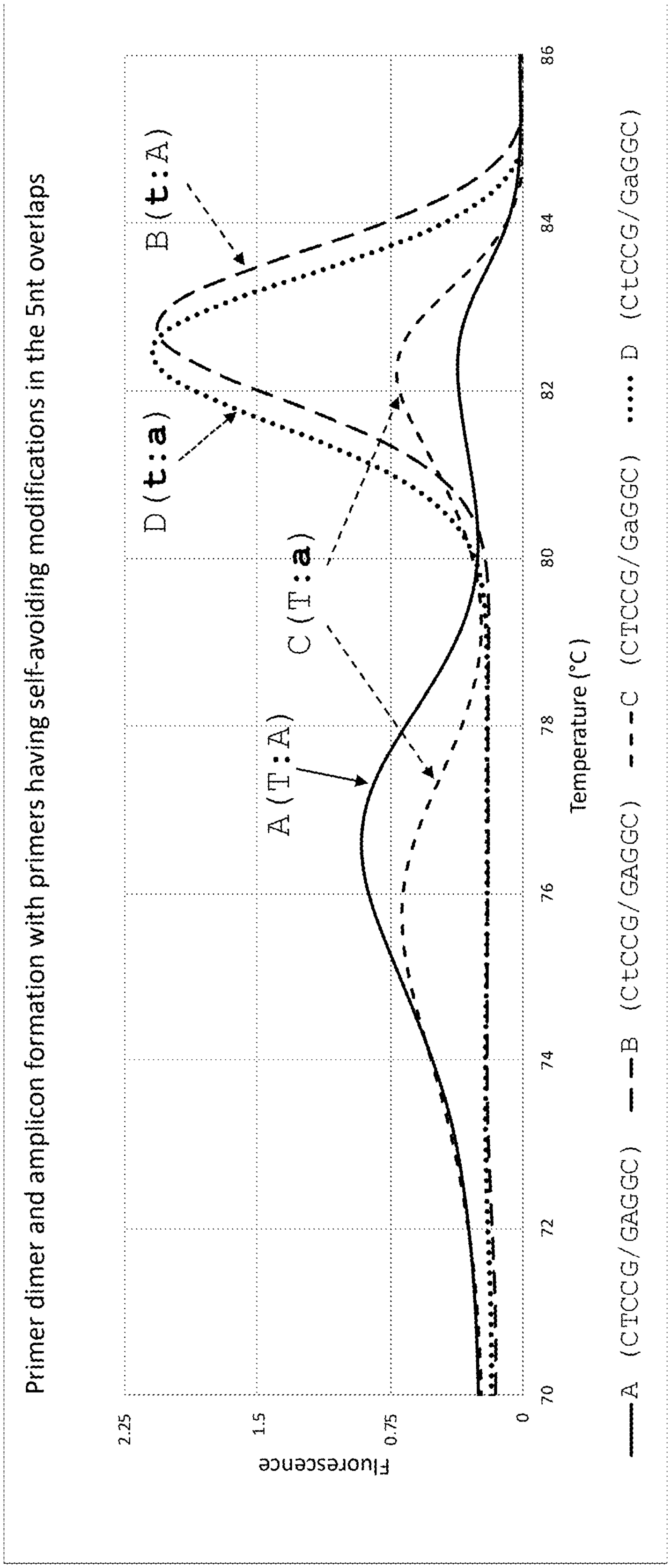
Figures 2, 7:
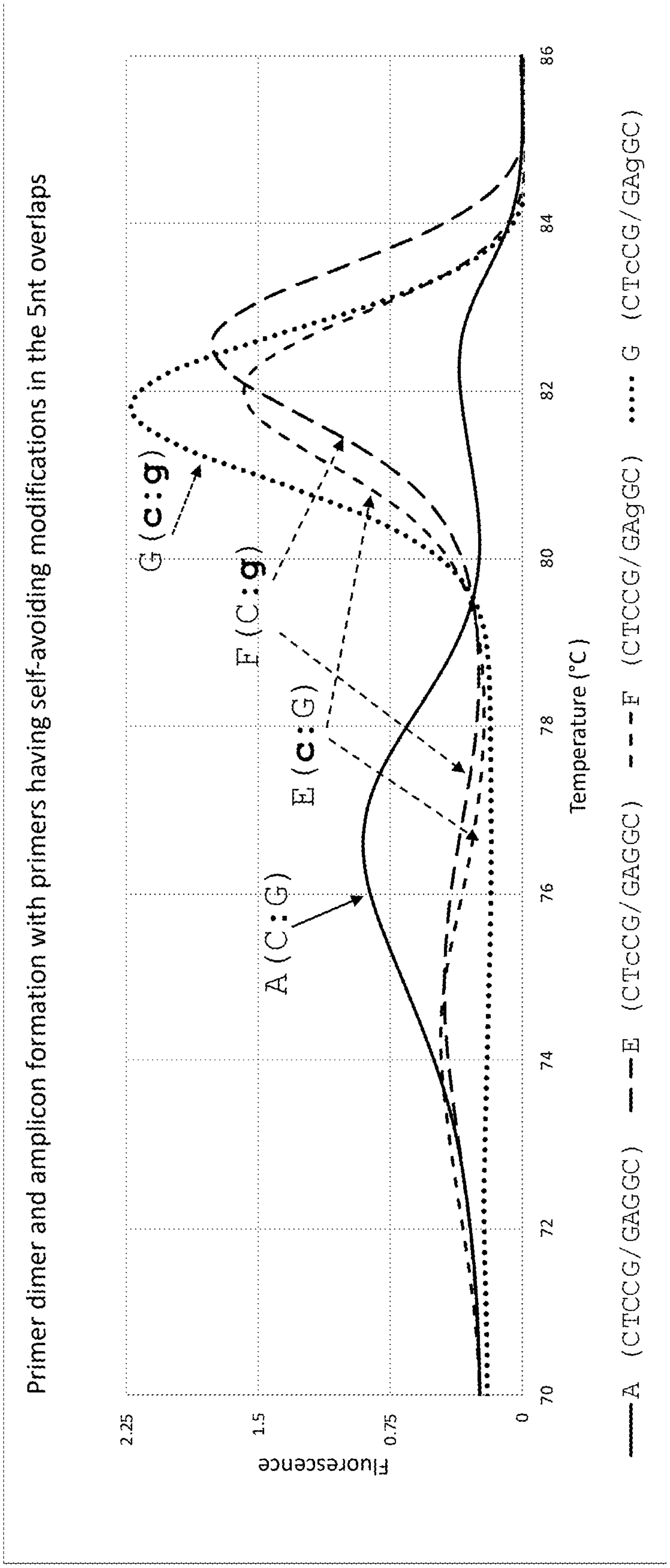

These surprising results correlate with the performance of t in PCR reactions, especially with six or more primers. Results show that this t works well in conjunction with a, g, and c analogs to eliminate artifact formation (Table 4, Table 5, FIG. 7, and FIG. 8). The order of preventing primer-primer interaction and eliminating primer dimers was experimentally observed to be: a:t>c:g>t:A>g:C≈c:G>a:T>>A:T>G:C (FIG. 7-1 and FIG. 7-2).

Notably, when primers contain one or two t, g, a, and c-modifications, fewer than ~2 cycles represent the variation in PCR efficiency of amplicon formation among all modified primers (Table 4, Table 5). Melting studies also correlate with a shift towards product formation compared to standard primers (FIG. 7-1 and FIG. 7-2).

Figure 9:
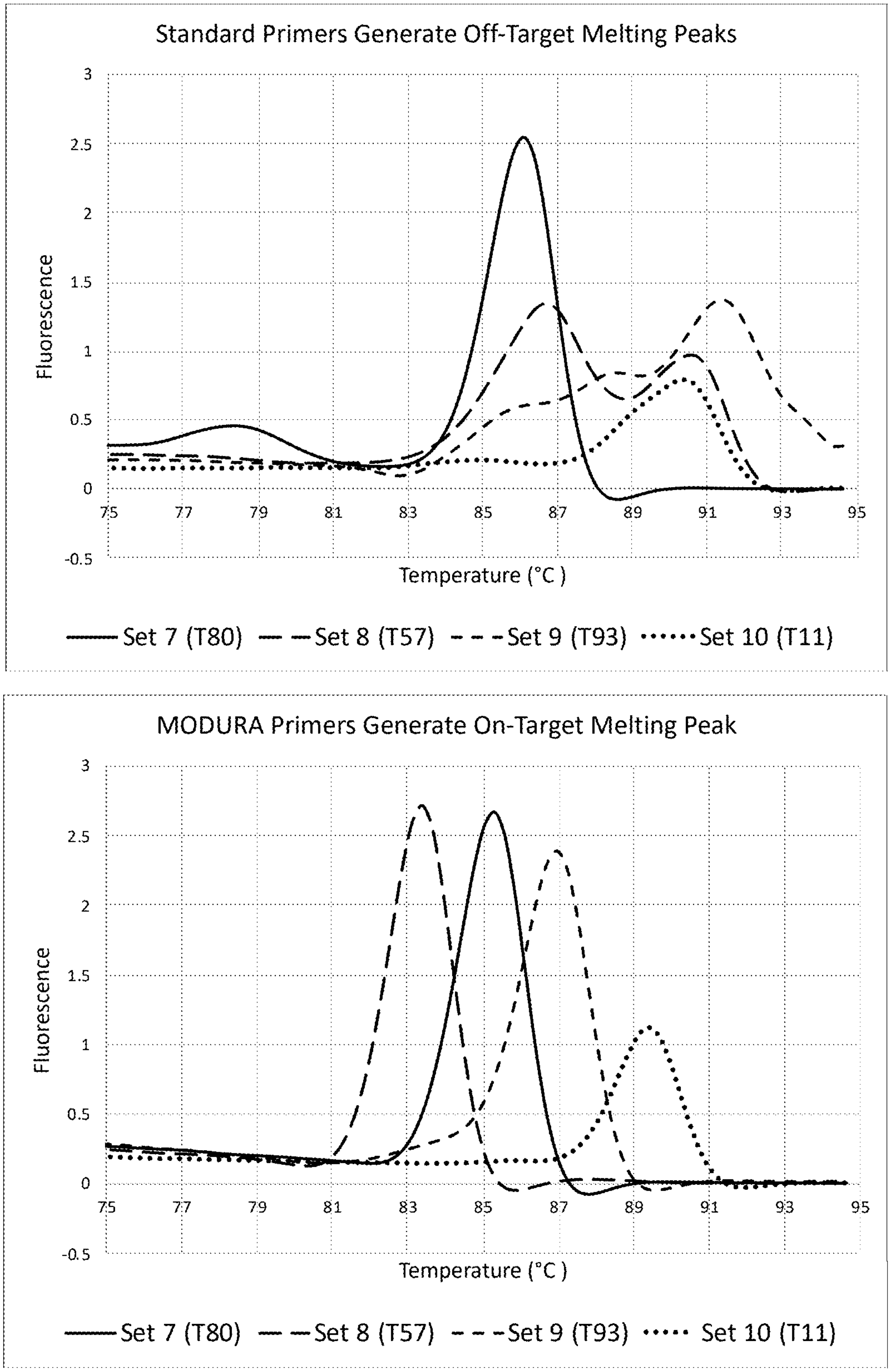
FIG. 9. Melting peaks of PCR on-target and off-target amplicons using standard primers or t, g, a, and c-modified primers (Example 8). In Example 8, each pair of standard primers or t, g, a, and c-modified primers was tested in PCR targeting human genomic DNA. PCR amplification was monitored by EvaGreen® dye and final PCR products were identified by melting peaking. Four pairs of standard primers (FIG. 9, left) are Set 7 (T80, SEQ ID NO: 118+SEQ ID NO: 120), Set 8 (T57, SEQ ID NO: 125+SEQ ID NO: 123), Set 9 (T93, SEQ ID NO: 127+SEQ ID NO: 126), and Set 10 (T11, SEQ ID NO: 128+SEQ ID NO: 130). Four pairs of t, g, a, and c-modified primers (FIG. 9, right) are Set 7 (T80, SEQ ID NO: 132+SEQ ID NO: 134), Set 8 (T57, SEQ ID NO: 139+SEQ ID NO: 137), Set 9 (T93, SEQ ID NO: 141+SEQ ID NO: 140), and Set 10 (T11, SEQ ID NO: 142+SEQ ID NO: 144). All standard primers were designed by the state-of-the-art bioinformatic software to avoiding the primer dimer formation. However, the results in Table 6-1 and Table 6-2 show that the "perfect" designed standard primers generate significantly off-targeting amplicons (significant sequencing reads for off-target amplicons and multiple melting peaks in FIG. 9, left). In contrast, t, g, a, and c-modified primers produce only desired PCR amplicon (single melting peak in FIG. 9, right).

Experiments also evaluated how t lowered off-target amplification. The incorporation of t, g, a, and c-modifications into standard primers that gave off-target amplicons surprisingly leads to more on-target amplification (Table 6-2 and FIG. 9). Subsequent simulant studies supported the theory that off-target hybrids and primer dimers can be generalized as partial priming events. The ability of t, g, a, and c-modifications to destabilize these undesired priming events deters their off-targeting formation and amplification, thereby facilitating the more efficient direction of PCR resources towards the formation of on-target amplicons (FIG. 9).

The oligonucleotide analogs of the instant invention can also be assembled as a library, which are mixtures of oligonucleotide analogs synthesized by solid phase synthesis where instead of adding a specific phosphoramidite at each step in a solid-state synthesis procedure, mixtures of phosphoramidites are added at each step. In description form, this means that the libraries have all four standard nucleotides at positions designated as "N" in the following sequences, and all four MODURA nucleotides at the positions designated X, for example: 5'-NN[X][X]NN-3', 5'-NN[X]N[X]NN-3', 5'-NN[X][X][X]NN-3', 5'-NNN[X]NN[X]NN-3', 5'-NN[X]NNN[X]NN-3', 5'-NN[X][X]NN[X]NN-3', or 5'-NN[X]NN[X][X]NN-3'.

Further, from the examples showing detailed procedures for making the iodo precursor of the pyridone nucleotide analog of the instant invention, the artisan understands how the palladium-catalyzed coupling will append essentially any alkene or alkyne, including those that carry biotin, fluorescent moieties, or other affinity and signaling tags. This is shown in FIG. 10 and the corresponding example, where trifluoroacetylated amino alkenes and alkynes are made.

EXAMPLES

Figure 3:
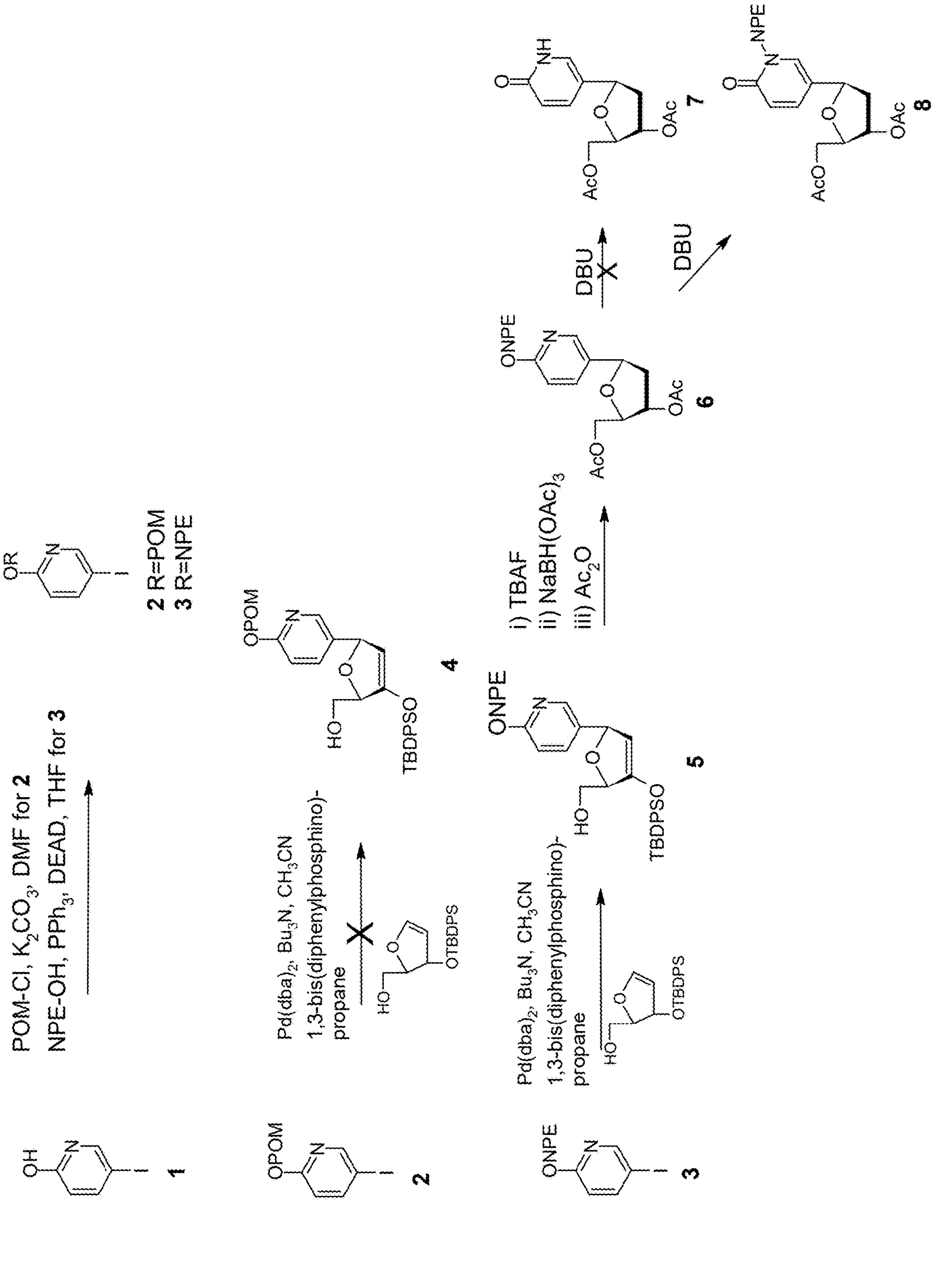
FIG. 3. Summary of failed attempts to synthesize 5-alkynyl-3-pyridin-2-one nucleosides in forms suitably protected for DNA synthesis (Example 1).

Example 1. Failed Attempts to Prepare 5-alkynyl-3-pyridin-2-one Nucleosides (FIG. 3)

The standard approach to make alkynyl and alkenyl heterocycles starts with an iodo-heterocycle, with the iodine substituent at the position where the alkynyl or alkenyl substituents are desired. This is followed by a palladium-catalyzed Heck coupling. As shown in FIG. 3, Heck coupling of POM-protected pyridone failed. However, upon further experimentation, Heck coupling with NPE-protected heterocycle gave the desired pyridone C-nucleoside (compound 5). Unfortunately, treatment with DBU to remove the NPE group gave an unexpected N-NPE derivative (compound 8). Thus, this overall synthesis also failed. These required the invention of a new synthetic route.

Example 2. Successful Procedure to Make a Protected Iodo-Nucleoside Precursor of t (FIG. 4)

After experimentation, the procedure summarized in FIG. 4 was developed. 2-(Benzyloxy)-5-iodo-pyridine (10)

To a stirred suspension of 60% NaH in mineral oil (1.05 g, 26.4 mmol) in DMF (30 mL) was added 2-bromo-5-iodopyridine (9) (5 g, 17.6 mmol) at 0° C., followed by addition of BnOH (2.18 mL, 21.1 mmol). The reaction mixture was warmed to room temperature over 3 h, then was heated at 75° C. overnight. The resulting mixture was poured into 1 N HCl (70 mL) and washed with diethyl ether (100 mL×3). The combined organic layers were dried ($Na_2SO_4$), filtered and evaporated. The residue was purified by silica gel column chromatography (Hex/EtOAc=8/1) to give 10 (4.5 g, 14.5 mmol, 82%). $^1H$ NMR (300 MHz, $CDCl_3$) δ 8.35 (d, 1H, J=1.8), 7.78 (dd, 1H, J=2.4 and 8.7), 7.32-7.46 (m, 5H), 6.64 (d, 1H, J=8.1), 5.34 (s, 2H).

2-Benzyloxy-5-[3'-O-(tert-butyldiphenylsilyl)-2'-deoxy-2',3'-didehydro-β-D-ribofuranos-1'-yl]-pyridine (12)

A mixture of $Pd(dba)_2$ (82 mg, 0.133 mmol) and 1,3-bis(diphenylphosphino)-propane (58 mg, 0.133 mmol) in $CH_3CN$ (15 mL) was stirred at room temperature for 30 min. This mixture was transferred to a solution of compound 10 (500 mg, 1.61 mmol), glycal (11) (470 mg, 1.33 mmol) and $Bu_3N$ (1.02 mL, 3.99 mmol) in $CH_3CN$ (25 mL) at room temperature. The reaction mixture was stirred overnight at 80° C., then filtered through a Celite pad (washed with EtOAc). The filtrate was evaporated and the residue was purified by silica gel column chromatography (Hex/EtOAc=3/1) to give 12 (600 mg, 1.12 mmol, 84%). $^1H$ NMR (300 MHz, $CDCl_3$) δ 7.91 (d, 1H, J=1.8), 7.66-7.81 (m, 5H), 7.20-7.50 (m, 11H), 6.63 (d, 1H, J=8.1), 5.53 (m, 1H), 5.32 (s, 2H), 4.72 (m, 1H), 4.27 (s, 1H), 3.83 (m, 2H), 1.06 (s, 9H).

2-Benzyloxy-5-(3'-dehydro-2',3'-di-deoxy-3'-oxo-β-D-ribofuranos-1'-yl]-pyridine (13)

To a stirred solution of 12 (600 mg, 1.12 mmol) in THF (15 mL) were added AcOH (0.28 mL) and 1M TBAF in THF (2.2 mL, 2.2 mmol) at 0° C. The reaction mixture was stirred for 10 min at 0° C. and evaporated. The residue was purified by silica gel column chromatography (Hex/EtOAc=1/1) to give 13 (210 mg, 0.7 mmol, 63%). $^1$H NMR (300 MHz, $CDCl_3$) δ 8.21 (d, 1H, J=2.1), 7.70 (dd, 1H, J=2.4 and 8.7), 7.32-7.47 (m, 5H), 6.85 (d, 1H, J=9.0), 5.40 (s, 2H), 5.17 (dd, 1H, J=6.0 and 11.1), 4.03 (m, 1H), 3.94 (m, 2H), 2.83 (dd, 1H, J=6.0 and 17.1), 2.49 (dd, 1H, J=11.1 and 18.0).

2-Benzyloxy-5-(2'-deoxy-β-D-ribofuranos-1'-yl]-pyridine (14)

To a stirred solution of 13 (210 mg, 0.7 mmol) in $CH_3CN$/AcOH (2/1, 18 mL) was added $NaBH(OAc)_3$ (223 mg, 1.05 mmol) at 0° C. The reaction mixture was stirred for 10 min at 0° C. and MeOH (5 mL) was added. The solvent was removed in vacuo and the residue was purified by silica gel column chromatography ($CH_2Cl_2$/MeOH=10/1) to give 14 (210 mg, 0.7 mmol, 99%). $^1$H NMR (300 MHz, DMSO-$d_6$) δ 8.12 (d, 1H, J=2.4), 7.70 (dd, 1H, J=2.4 and 8.7), 7.29-7.43 (m, 5H), 6.82 (d, 1H, J=9.0), 5.32 (s, 2H), 5.05 (d, 1H, J=3.0), 4.95 (dd, 1H, J=5.1 and 10.5), 4.75 (m, 1H), 4.18 (m, 1H), 3.73 (m, 1H), 3.41 (m, 2H), 1.98 (m, 1H), 1.75 (m, 1H).

2-Benzyloxy-5-(3',5'-di-O-acetyl-2'-deoxy-β-D-ribofuranos-1'-yl]-pyridine (15)

To a stirred solution of 14 (210 mg, 0.7 mmol) in pyridine (15 mL) were added $Ac_2O$ (0.2 mL, 2.1 mmol) and catalytic amount of DMAP at room temperature. The reaction mixture was stirred for 1 h at room temperature and evaporated. The residue was purified by silica gel column chromatography (Hex/EtOAc=1/1) to give 15 (250 mg, 0.65 mmol, 93%). $^1$H NMR (300 MHz, $CDCl_3$) δ 8.13 (d, 1H, J=2.7), 7.58 (dd, 1H, J=2.4 and 8.7), 7.31-7.44 (m, 5H), 6.80 (d, 1H, J=8.1), 5.37 (s, 2H), 5.22 (d, 1H, J=6.3), 5.04 (dd, 1H, J=4.8 and 7.5), 4.20-4.38 (m, 3H), 2.28 (m, 1H), 2.12, 2.10 (2s, 6H), 2.01 (m, 1H).

5-(3',5'-Di-O-acetyl-2'-deoxy-β-D-ribofuranos-1'-yl]-2-pyridone (16)

Compound 15 (1.33 g, 3.45 mmol) was dissolved in EtOH (120 mL) and 10% Pd/C (130 mg) was added. The reaction mixture was degassed and stirred for 3 h under $H_2$ atmosphere. The catalyst was removed by filtration and washed with MeOH. The filtrate was evaporated and the residue was purified by silica gel column chromatography ($CH_2Cl_2$/MeOH=10/1) to give 16 (920 mg, 3.12 mmol, 90%). $^1$H NMR (300 MHz, $CDCl_3$) δ 7.45 (dd, 1H, J=2.4 and 9.3), 7.36 (d, 1H, J=2.4), 6.59 (d, 1H, J=9.3), 5.18 (d, 1H, J=6.9), 4.85 (dd, 1H, J=5.1 and 11.4), 4.16-4.33 (m, 3H), 2.21 (m, 1H), 2.11, 2.10 (2s, 6H), 1.95 (m, 1H).

5-(3',5'-di-O-acetyl-2'-deoxy-β-D-ribofuranos-1'-yl]-3-iodo-2-pyridone (17)

A mixture of 16 (250 mg, 0.85 mmol), $I_2$ (268 mg, 1.06 mmol) and CAN (466 mg, 0.85 mmol) in $CH_3CN$ (10 mL) was stirred overnight at room temperature. The reaction mixture was evaporated, diluted with EtOAc (100 mL) and washed with 10% $Na_2S_2O_3$ (15 mL) and brine (20 mL). The organic layer was organic layers were dried ($Na_2SO_4$), filtered and evaporated. The residue was purified by silica gel column chromatography ($CH_2Cl_2$/MeOH=12/1) to give 17 (264 mg, 0.63 mmol, 74%). $^1$H NMR (300 MHz, $CDCl_3$) δ 8.13 (d, 1H, J=2.1), 7.49 (d, 1H, J=1.8), 5.19 (d, 1H, J=6.3), 4.83 (dd, 1H, J=5.4 and 10.5), 4.18-4.33 (m, 3H), 2.22 (m, 1H), 2.15, 2.11 (2s, 6H), 2.00 (m, 1H).

Example 3. Synthesis of Protected Phosphoramidite of Ethynyl Derivative (FIG. 5)

FIG. 5 shows synthesis of 3-ethynyl-2-pyridone phosphoramidite 22. Sonogashira coupling of 3-iodo-2-pyridone derivative 18 with triisopropylsilylacetylene gave the 3-ethynyl derivative 19. Introduction of a POM group using POM-Cl and $K_2CO_3$ in DMF gave the mixture of N-alkylated 20a and O-alkylated 20b in ratio of 3/1. This was protected with dimethoxytrityl chloride. Products were separated by column chromatography to give N-protected 21. Phosphitylation of 21 under Ludwig-Eckstein conditions gave phosphoramidite 22. This was suitable for standard solid phase synthesis.

5-(2'-Deoxy-β-D-ribofuranos-1'-yl)-3-(triisopropylsilylethynyl)-2-pyridone (19)

To a stirred solution of 18 (260 mg, 0.77 mmol) in DMF (10 mL) were added CuI (30 mg, 0.16 mmol), $Pd(PPh_3)_4$ (86 mg, 0.077 mmol), $Et_3N$ (0/27 mL, 1.9 mmol) and triisopropylsilylacetylene (0.69 mL, 3.08 mmol) at room temperature. The reaction mixture was stirred overnight at room temperature and evaporated. The residue was purified by silica gel column chromatography ($CH_2Cl_2$/MeOH=20/1 to 5/1) to give 19 (195 mg, 0.5 mmol, 65%). $^1$H NMR (300 MHz, DMSO-$d_6$) δ11.86 (s, 1H), 7.63 (d, 1H, J=2.4), 7.40 (s, 1H), 5.00 (d, 1H, J=4.2), 4.73-4.78 (m, 2H), 4.13 (m 1H), 3.66 (m, 1H), 3.39 (m, 2H), 1.88 (m, 1H), 1.76 (m, 1H), 1.05 (s, 21H).

5-(2'-Deoxy-β-D-ribofuranos-1'-yl)-N-(pivalovloxymethyl)-3-(triisopropylsilylethynyl)-2-pyridone (20a) and 5-(2'-Deoxy-β-D-ribofuranos-1'-yl)-2-(pivaloyloxymethoxy)-3-(triisopropylsilylethynyl)-pyridine (20b)

To a stirred solution of 19 (195 mg, 0.5 mmol) in DMF (8 mL) were added $K_2CO_3$ (207 mg, 1.5 mmol) and chloromethyl pivalate (108 μL, 0.75 mmol) at room temperature. The reaction mixture was stirred overnight at room temperature, filtered, and the residue was washed with EtOAc. The filtrate was evaporated and the residue was purified by silica gel column chromatography ($CH_2Cl_2$/MeOH=10/1) to give the mixture of 20a and 20b (170 mg, 0.34 mmol, 68%). 20a: $^1$H NMR (300 MHz, $CDCl_3$) δ 7.56 (d, 1H, J=2.4), 7.51 (d, 1H, J=2.1), 5.88 (d, 1H, J=9.3), 5.82 (d, 1H, J=9.6), 4.87 (m, 1H), 4.46 (m, 1H), 3.96 (m, 1H), 3.70-3.85 (m, 2H), 2.14 (m 1H), 1.95 (m, 1H), 1.18 (s, 9H), 1.13 (s, 21H).

5-[2'-Deoxy-5'-O-(dimethoxytrityl)-β-D-ribofuranos-1'-yl]-N-(pivaloyloxymethyl)-3-(triisopropylsilylethynyl)-2-pyridone (21)

The mixture of 20a and 20b (170 mg, 0.34 mmol) was dissolved in $CH_2Cl_2$ (10 mL) and $Et_3N$ (95 μL, 0.68 mmol)

and DMTCl (136 mg, 0.4 mmol) were added at room temperature. The reaction mixture was stirred at room temperature for 1 h and evaporated. The residue was purified by silica gel column chromatography (Hex/EtOAc=1/1) to give 21 (130 mg, 0.16 mmol, 47%). $^1H$ NMR (300 MHz, $CDCl_3$) δ 7.59 (d, 1H, J=1.5), 7.17-7.47 (m, 10H), 6.80 (m, 2H), 5.81 (d, 1H, J=9.9), 5.75 (d, 1H, J=9.9), 4.84 (m, 1H), 4.42 (m, 1H), 4.00 (m, 1H), 3.21-3.33 (m, 2H), 2.13 (m, 1H), 2.01 (m, 1H), 1.16 (s, 9H), 1.10 (s, 21H)

5-[2'-Deoxy-3'-O-(2-cyanoethyl-N,N-diisopropylamino)-phosphino-5'-O-(dimethoxytrityl)-β-D-ribofuranos-1'-yl]-N-(pivaloyloxymethyl)-3-(triisopropylsilylethynyl)-2-pyridone (22)

To a stirred solution of 21 (590 mg, 0.73 mmol) in $CH_2Cl_2$ (20 mL) were added N,N-diisopropylethylamine (261 μL, 1.5 mmol) and 2-cyanoethyl-N,N-diisopropylchlorophosphite (245 μL, 1.1 mmol) at 0° C. The reaction mixture was warmed to room temperature, stirred for 1 h and evaporated. The residue was purified by column chromatography (neural silica gel, Hex/EtOAc=7/3) to give 22 (500 mg, 0.5 mmol, 68%). $^1H$ NMR (300 MHz, $CDCl_3$) δ7.58 (m, 1H), 7.44 (m, 1H), 7.12-7.69 (m, 9H), 6.73 (m, 4H), 5.70 (m, 2H), 4.79 (m, 1H), 4.43 (m, 1H), 4.07 (m, 1H), 3.46-3.77 (m, 10H), 3.15-3.26 (m, 2H), 2.53 (m, 1H), 2.35 (m, 1H), 2.12-2.28 (m, 1H), 1.90-1.98 (m, 1H), 0.92-1.22 (m, 42H); $^{31}P$ NMR (121 MHz, $CDCl_3$) δ 147.94, 147.85.

Example 4. Synthesis of 3-propynyl-5-(1'-beta-D-2'-deoxyribofuranosyl)-pyridin-2-one (FIG. 6)

3-Propynyl-2-pyridone phosphoramidite 26 was synthesized as shown in FIG. 6. First, pyrid-2-one 18 was selectively N-alkylated to give N-protected 23, with less than 10% of O-alkylated product formed. The Sonogashira coupling with propyne, followed by 5'-tritylation and phosphitylation gave the phosphoramidite 26.

5-(2'-Deoxy-β-D-ribofuranos-1'-yl)-3-iodo-N-(pivalovloxymethyl)-2-pyridone (23)

To a stirred solution of 18 (450 mg, 1.33 mmol) in DMF (15 mL) were added $K_2CO_3$ (553 mg, 4.0 mmol) and chloromethyl pivalate (0.29 mL, 2.0 mmol) at room temperature. The reaction mixture was stirred overnight at room temperature, filtered and washed with EtOAc. The filtrate was evaporated and the residue was purified by silica gel column chromatography ($CH_2Cl_2$/MeOH=20/1 to 10/1) to give 23 (315 mg, 0.7 mmol, 53%). $^1H$ NMR (300 MHz, $CDCl_3$) δ 8.00 (d, 1H, J=2.4), 7.57 (d, 1H, J=1.8), 5.83 (m, 2H), 4.87 (m, 1H), 4.45 (m, 1H), 3.96 (m, 1H), 3.72-3.80 (m, 2H), 2.13 (m, 1H), 1.92 (m, 1H), 1.18 (s, 9H).

5-(2'-Deoxy-β-D-ribofuranos-1'-yl)-N-(pivalovloxymethyl)-3-(1-propyiyl)-2-pyridone (24)

To a stirred solution of 23 (315 mg, 0.7 mmol) in DMF (8 mL) were added CuI (27 mg, 0.14 mmol), $Pd(PPh_3)_4$ (78 mg, 0.07 mmol), $Et_3N$ (0.24 mL, 1.75 mmol) and 4% propyne in DMF (2.8 mL, 2.8 mmol) at room temperature. The reaction mixture was stirred overnight at room temperature and evaporated. The residue was purified by silica gel column chromatography (EtOAc to EtOAc/MeOH=9/1) to give 24 (250 mg, 0.68 mmol, 97%). $^1H$ NMR (300 MHz, $CDCl_3$) δ 7.50 (s, 1H), 7.47 (d, 1H, J=2.1), 5.80 (m, 2H), 4.86 (m, 1H), 4.42 (m, 1H), 3.95 (m, 1H), 3.69-3.82 (m, 2H), 2.12 (m, 1H), 2.10 (s, 3H), 1.9 (m, 1H), 1.17 (s, 9H).

5-[2'-Deoxy-5'-O-(dimethoxytrityl)-β-D-ribofuranos-1'-yl]-N-(pivalovloxymethyl)-3-(1-propynyl)-2-pyridone (25)

To a stirred solution of 24 (250 mg, 0.68 mmol) in $CH_2Cl_2$ (15 mL) were added $Et_3N$ (190 μL, 1.36 mmol) and DMTCl (272 mg, 0.8 mmol) at room temperature. The reaction mixture was stirred at room temperature for 1 h and evaporated. The residue was purified by silica gel column chromatography (Hex/EtOAc=3/7) to give 25 (360 mg, 0.54 mmol, 80%). $^1H$ NMR (300 MHz, $CDCl_3$) δ 7.57 (d, 1H, J=2.4), 7.20-7.42 (m, 10H), 6.81 (m, 4H), 5.74 (m, 2H), 4.84 (m, 1H), 4.42 (m, 1H), 3.98 (m, 1H), 3.78 (s, 6H), 3.32 (m, 1H), 3.17 (m, 1H), 2.09 (m, 1H), 2.02 (s, 3H), 1.88 (m, 1 h), 1.16 (s, 9H).

5-[2'-Deoxy-3'-O-(2-cyanoethyl-N,N-diisopropylamino)-phosphino-5'-O-(dimethoxytrityl)-p-D-ribofuranos-1'-yl]-N-(pivalovloxymethyl)-3-(1-propynyl)-2-pyridone (26)

To a stirred solution of 25 (360 mg, 0.54 mmol) in $CH_2Cl_2$ (15 mL) were added N,N-diisopropylethylamine (191 μL, 1.1 mmol) and 2-cyanoethyl-N,N-diisopropylchlorophosphite (180 μL, 0.81 mmol) at 0° C. The reaction mixture was warmed to room temperature, stirred for 3 h and evaporated. The residue was purified by column chromatography (neural silica gel, Hex/EtOAc=1/1) to give 26 (260 mg, 0.3 mmol, 56%). $^1H$ NMR (300 MHz, $CDCl_3$) δ 7.62 (m, 1H), 7.19-7.44 (m, 10H), 6.80 (m, 4H), 5.74 (m, 2H), 4.84 (m, 1H), 4.15 (m, 1H), 3.56-3.78 (m, 10H), 3.21-3.26 (m, 2H), 2.59 (m, 1H), 2.42 (m, 1H), 2.17-2.29 (m, 1H), 1.98-2.04 (m, 4H), 1.08-1.30 (m, 21H); $^{31}P$ NMR (121 MHz, $CDCl_3$) δ 148.05, 147.98.

Table 1. Synthesize Oligonucleotides Containing a, k, c, t, and 2-Thiothymidine, with Measurements of the Melting Temperatures of Oligonucleotide Duplexes Oligonucleotides containing g, a, c, and t were synthesized from their corresponding protected phosphoramidite precursors on Mermade 12 instruments, using standard phosphoramidite methods with minor changes to the coupling time of the g, a, c, and t phosphoramidites (1 min). The solid support was a Mermade style column packed with controlled pore glass (CPG) at 1000 Å pore size. Oligonucleotides were synthesized as either DMT-on or DMT-off at the end of the synthesis. DMT-off oligonucleotides were deprotected in aqueous ammonium hydroxide (28-33% $NH_3$ in water) at either 65° C. for 3 hours, 55° C. overnight, or 25° C. for over 16 hours. Then, oligonucleotides were purified by ion-exchange HPLC (Dionex DNAPac PA-100, 22×250 column), and desalted over SepPak C18 cartridges (Waters Corp., Milford, MA). Oligonucleotides synthesized as DMT-on were deprotected using the same method, followed by purification on Glen-Pak cartridges (GlenResearch, Sterling, VA). The purity of each oligonucleotide was analyzed by analytical ion-exchange HPLC (Dionex DNAPac PA-100, 2×250 column). The oligonucleotides were sent out for ESI mass spectrometry (Novatia LLC, Newtown, PA) to confirm their molecular weights. All sequences of oligonucleotides with or without g, a, c, and t modifications are listed in Table 1.

Table 2. Melting Temperatures (° C.) of the Double-Stranded DNA Containing Standard and g, a, c, and t Nucleotides The novel 3-(1-propynyl)-2-pyridone analog of thymidine (t in SEQ ID NO: 16 to SEQ ID NO: 24, SEQ ID NO: 65, and SEQ ID NO: 66, Table 1-1) was compared with the previous 2-thiothymidine (2-thio t in SEQ ID NO: 50 and SEQ ID NO: 58, Table 1-1) in melting studies for match and mismatch pairs (Table 2).

The melting temperature of various oligonucleotide duplex (1 μM, Table 2-1 and Table 2-2) were measured in 1×PCR buffer (50 mM Tris-HCl, pH 8.3, 0.5 μg/μL BSA, 3 mM $MgCl_2$) with 1×EvaGreen® (Biotium, NC05211). Each duplex was measured 3 times in duplicate and run in parallel on a 96-well plate. Duplicate sample reads were averaged with an average run deviation of 0.6±0.3° C. for Table 2-1 and 0.4±0.2° C. for Table 2-2.

Compared to the standard T:A base pair, the t:A pair decreases the $T_m$ by about 1.2° C.±0.9° C., T: a decreases by 1.1° C.±0.9° C., and t:a decreases the $T_m$ by 5.2° C.±2.5° C. These delta $T_m$s were seen when the t and a modifications were located in the last 5 bases of 14 nucleotide double-stranded DNA (Table 2-1).

Melting temperatures of double-stranded DNA containing N:T or N:t pair were studied with all possible mismatches (G:T, g:T, C:T, T:T vs. G:t, g:t, C:t, T:t, Table 2-2). The delta $T_m$ between N:T and N:t pair (e.g. G:T vs. G:t; C:T vs. C:t; T:T vs. T:t, etc.) was, in average, within ±0.5° C. This indicates that the t has the same mis-match discrimination as standard T (Table 2-2).

The melting temperatures of the 15mer double-stranded DNA containing the X:Y pairs in the middle (position 8, Table 1-1, SEQ ID NO: 49 to SEQ ID NO: 66), where all the possible base pairs were tested as either standard:standard, MODURA:standard, or MODURA:MODURA (Table 2-3 and Table 2-4). The melting temperature of duplex (1 μM) was measured in 1×PCR buffer (50 mM Tris-HCl, pH 8.3, 0.5 μg/μL BSA, 3 mM $MgCl_2$) with 1×EvaGreen® (Biotium, NC05211). Each duplex was measured 3 times in duplicate and run in parallel on a 96-well plate. Duplicate sample reads were averaged with an overall average run deviation of 0.2±0.2° C.

The double strand DNA containing the X:Y pairs are as follows: 5'-ACCAAGCXATCAAGT-3' (SEQ ID NO: 49 to SEQ ID NO: 56 and SEQ ID NO: 65) and 3'-TGGTTCGYTAGTTCA-5' (SEQ ID NO: 57 to SEQ ID NO: 64 and SEQ ID NO:66), where X=T, t (2-thiothymidine versus t), A, a, C, c, G, g; Y=T, t (2-thiothymidine versus t), A, a, C, c, G, g.

The results are shown in Table 2-3 and Table 2-4. Summarizing the results:

(1) The t has better mis-match discrimination, with the following observed duplex stabilities when incorporated into double-stranded DNA.

(2) Duplexes with t pairing with A (t:A) have a ~2.4° C. average lower $T_m$ than duplexes with standard T pairing with A (T:A).

(3) Duplexes with t:a pair have an average lower $T_m$ than analogous duplexes with g:c pair when compared to T:A as the reference (−7.0 vs. −3.5° C., Table 2-4).

(4) The A:T base pair makes duplexes more stable than with a corresponding a:T base pair by ~1.4±0.2° C.

(5) The T:A base pair makes duplexes more stable than the t:A base pair by ~2.6±0.4° C.

(6) The C:G base pair makes duplexes more stable than the c:G base pair by ~2.9±0.3° C.

(7) The G:C base pair makes duplexes more stable than the g:C base pair by ~4.4±0.2° C.

(8) Duplexes containing A:T pair are more stable than those with a:t pair by ~7.2±0.2° C. on average.

(9) Duplexes containing G:C pair are more stable than those with g:c pair by ~6.8 0.1° C. on average.

(10) These $T_m$ comparisons show that the 2-thiothymidine:A pair gave higher $T_m$'s than T:A in duplex DNA by ~0.75±0.2° C. on average (Table 2-3).

(11) Further, DNA duplexes containing the t:A pair have a lower $T_m$ than the T:A pair by ~2.6±0.4° C., while duplexes containing a t:a pair greatly decreases the $T_m$ by ~7.2±0.2° C. than standard DNA duplexes containing a T:A pair; an even larger self-avoiding impact than seen with the g:c pair (~6.8±0.1° C.), to destabilize duplex DNA (Table 2-4).

(12) Last, surprisingly, the melting temperatures of the mismatched pair between t with other bases (t:Y, Y=a, T, t, G, g, C, c), on average, are 2.4° C. lower than T:Y base pair (Table 2-4). This indicates that t offers better mismatch discrimination than standard T, especially for T:G mismatches (t:G lowering $T_m$ by about 3.5° C. than T:G, Table 2-4).

Table 3. Evaluated the Primer Dimer Formation of Standard Primers and MODURA-Modified Primers in Non-Template Control (NTC).

To illustrate the effect of primers modified with self-avoiding components (t and a) to diminish or eliminate primer dimers, an experiment was designed to use primers (192 primers) adopted from a 96-plex PCR assay published in a recent paper in Nature Communications[14]. Next-generation sequencing results shown over 90% of total sequencing reads came from primer dimers and vast majority of primer dimers were caused by primers having perfect complementary overlap at 3' ends. We choose two primer sets (Set 1 and Set 2) from this paper containing either five or four nucleotides overlaps (5 nt or 4 nt overlaps in the 3' region of the primers, Table 3-1). These primer sets were tested in a "No Template Control "(NTC) PCR with various DNA polymerases to evaluate the dimer prevention obtained with 2-thiothymidine compared to t when pairing with standard A or a to form t:A or t:a in the 3' overlap region (Table 3-2).

Set 1 and Set 2 primers were tested in PCR with QuantiTect® multiplex PCR kit (Qiagen, Cat #204543), Takara® One Step PrimeScript™ III RT-PCR Kit (Takara Bio, RR600B), and TaqPath® 1-Step RT-qPCR Master Mix (ThermoFisher, A15299) in the "No Template Control" (NTC) reactions, where primer dimers are the only likely products (Table 3-2). Dimer formation and cycle threshold (Ct) was monitored by EvaGreen® dye, with an earlier Ct indicates a worse primer dimer formation. As the results shown in Table 3-2, all standard primers generated primer dimers with three polymerases tested. Standard primers (Set 1 primers) having 5 nt overlap (SEQ ID NO: 67 pairs with SEQ ID NO: 68) gave primer dimer ~10 cycles earlier than standard primers (Set 2 primers) having 4 nt overlap (SEQ ID NO: 69 pairs with SEQ ID NO: 70) for all three polymerases. With Set 1 and Set 2 standard primers, TaqPath® RT-PCR kit generated earlier primer dimer (Ct of 11.1 for Set1-5 overlap and 24.4 for Set2-4 overlap) than Takara® RT-PCR kit (Ct of 16.8 for Set1-5 overlap and 25.3 for Set2-4 overlap) and QuantiTect® PCR kit (Ct of 22.1 for Set1-5 overlap and 35.7 for Set2-4 overlap, Table 3-2).

Surprisingly, replacing only one T with t (in SEQ ID NO: 72 and SEQ ID NO: 76) to give t:A in the overlap regain (SEQ ID NO: 72 pairs with SEQ ID NO: 68 and SEQ ID NO: 76 pairs with SEQ ID NO: 69) deterred primer dimer formation for all three polymerases (Table 3-2). Using Ct of the standard primers containing base pair T:A as a reference, t:A pair caused the delay of the Ct by ~2.4 up to 13 cycles than standard primer pair T:A (in SEQ ID NO: 67 pairs with SEQ ID NO: 68 and SEQ ID NO: 69 pairs with SEQ ID NO: 70).

Furthermore, matching t-modified primers (SEQ ID NO: 72 and SEQ ID NO: 76) with a-modified primers (SEQ ID NO: 73 and SEQ ID NO: 74), the primer pairs containing t:a in the overlap region (SEQ ID NO: 72+SEQ ID NO: 73 and SEQ ID NO: 76+SEQ ID NO: 74) delayed Ct by ~5 cycles, modest self-avoidance, to 26 cycles (extremely strong self-avoidance) for all three polymerases (Table 3-2).

Without being bound by theory, the capacity of t and a modifications to lower primer dimer formation may correspond to the destabilization of the partially primed (annealed) primer pairs in the 3'-overlap region. This instability can be described as a factor of $T_m$, as a lower $T_m$ of t:a is equivalent to a less stable duplex (Table 2).

We then compared the effectiveness of primer-dimer prevention of yielded by 2-thiothymidine versus t. A comparative analysis of t (in SEQ ID NO: 72 and SEQ ID NO: 76) versus 2-thiothymidine (in SEQ ID NO: 71 and SEQ ID NO: 75) was done when paired against standard A (in SEQ ID NO: 68 and SEQ ID NO: 69) and a (in SEQ ID NO: 73 and SEQ ID NO: 74). The formation of primer dimer was monitored by EvaGreen® dye (Table 3-2). These experiments showed that t (in SEQ ID NO: 72 and SEQ ID NO: 76) effectively prevents primer dimer formation, outperforming 2-thiothymidine in this capacity (in SEQ ID NO: 71, SEQ ID NO: 75). 2-Thiothymidine pairing with A in the overlap region actually accelerated primer dimer formation (SEQ ID NO: 71+SEQ ID NO: 68 and SEQ ID NO: 75+SEQ ID NO: 69), with Ct ~1 up to 7 cycles earlier than standard T:A pair. While 2-thiothymidine:a pairs in Set 2 primers having 4 nt overlap (in SEQ ID NO: 71+SEQ ID NO: 73 and SEQ ID NO: 75+SEQ ID NO: 74) managed to delay primer dimer formation by ~1 up to 5 cycles. Sometimes, 2-thiothymidine:a pairs in Set 1 primers having 5 nucleotide overlap encourage primer dimer formation by ~1 to 3 cycles (Table 3-2).

These primer dimer results in PCR without template (NTC) correlate with melting study results. Here, t has a lower $T_m$ when paired with a, and thus is a stronger deterrent of primer dimer formation (Table 2-4 and Table 3-2). In contrast, 2-thiothymidine paired with standard adenine has a higher $T_m$ compared to the standard pair T:A, and thus encourage primer-dimer formation (Table 2-3 and Table 3-2).

These data drive the following conclusions. The t of the instant invention is shown to be effective at deterring primer dimer formation in the PCR without template (NTC). Comparing to the Ct of standard primers with T:A, the overlaps containing t:A delay Ct by ~2.4 up to 13 cycles, while the overlaps containing t:a delay Ct by ~5 up to 26 cycles (Table 3-2).

2-Thiothymidine, the self-avoiding replacement for thymidine that is taught in the art, in fact encourages primer dimer formation, producing dimers ~1 up to 7 cycles earlier than seen with standard primers with T:A pair. The results are consistent with incubations where DNA polymerases are included with a reverse transcriptase (RT), like Takara® and TaqPath® RT-PCR kit and those that do not, like QuantiTect®.

These results correlate well with melting results where t contributes to a lower $T_m$ and thus is a stronger deterrent of primer dimer formation. As 2-thiothymidine paired with standard adenine give duplexes with a higher $T_m$ compared to standard T paired with adenine (T:A), it can encourage primer dimer formation (Table 2-3 and Table 3-2).

Table 4. Evaluated the PCR Efficiency of Standard Primers and MODURA-Modified Primers Using Nonspecific Probe (EvaGreen® Dye)

To assess the utility of t, it is essential to evaluate its efficacy in conjunction with other self-avoiding analogs (a, c, and g) within a PCR reaction involving a target template. To facilitate this evaluation, we designed synthetic templates that have been engineered to include regions of perfect complements to the forward and reverse primers (Sets3, Sets4, Sets5, and Sets6) as outlined in Table 4-1. Each set of forward and reverse primers was designed to have four, five, or six nucleotides overlap at their 3' ends. These overlaps are likely to cause primer dimers even in the presence of target. The formation of primer dimer and desired PCR amplicon can be monitored during PCR using nonspecific EvaGreen® dye (Table 4-2 and Table 4-3) and distinguished using melting curves analysis in the end of PCR (FIG. 7). Furthermore, these synthetic templates feature a designated area for a TaqMan® probe with a red-color reporting dye, enabling precise monitoring of amplicon formation to gauge PCR efficiency accurately (Table 5 and FIG. 8). Using both the specific TaqMan® probe with red color and nonspecific fluorescence dye with green color (EvaGreen®) gave additional insights into the competition between amplicon formation and primer dimer formation (FIG. 7).

To evaluate the primer dimer and PCR amplicon formation of primers having 5 nt overlap at their 3' ends (set3-5 overlap, Table 4-1), primers with or without self-avoiding analog modifications (t, a, c, or g, Table 4-2) were used to amplify various among of templates ($10^6$-$10^3$ copies of target per reaction) using either Takara® RT-PCR kit or Platinum II Taq Hot-Start DNA polymerase (ThermoFisher, Cat #14966001). The results in Table 4-2 show standard primers (SEQ ID NO: 77+SEQ ID NO: 79) generated primer dimers at cycle 8 for all target concentrations including NTC with Takara® Taq (Table 4-2). With Platinum II polymerase, standard primers (SEQ ID NO: 77+SEQ ID NO: 79) gave primer dimer at cycle ~21 for low target concentrations ($10^3$ copies of target per reaction) and NTC (Table 4-2). Using EvaGreen®, any delta Ct within one cycle between NTC and target is indicative of a mixture of primer dimer and amplicon formation (Table 4-2). Melting curve analysis in the end of PCR provided a qualitative assessment of primer dimer ($T_m$~74° C.-79° C.) and amplicon product ($T_m$~81° C.-84° C.) (FIG. 7-1 and FIG. 7-2).

Compared to standard primers, primers modified with t, a, c, or g in the overlap region slow the formation of dimer in NTC and enable target amplification (Table 4-2 and Table 4-3). The ability of MODURA modification to prevent primer dimer is somewhat dependent on the polymerase. Platinum II Taq polymerase gives less dimer than Takara Taq in RT-PCR kit (Table 4-2). The MODURA analogs have different impact for preventing primer dimer. For instance, with Platinum II Taq, primers having T:a pair or C:g pair in the overlap region (SEQ ID NO: 77+SEQ ID NO: 91 or SEQ ID NO: 77+SEQ ID NO: 92) have a Ct of 23.3 for NTC, 2 cycles delayed relative to standard T:A pair (in SEQ ID NO: 77+SEQ ID NO: 79). Overlaps containing c:G pair (in SEQ ID NO: 90+SEQ ID NO: 79) and c:g pair (in SEQ ID NO: 90+SEQ ID NO: 92) have Cts of 25.0 and 28.3 for NTC, respectively, these Cts are ~4 up to 7 cycles delayed than the reference C:G pair (Ct of 21.2). Surprisingly, overlaps containing t:A pair (in SEQ ID NO: 89+SEQ ID NO: 79) has a Ct of 36.4 for NTC, and t:a pair (in SEQ ID NO: 89+SEQ ID NO: 91) has No Signal (NS, Table 4-2) at all for NTC using Platimun II Taq.

The results in Table 4-2 shown the ability of t, a, c, andg modifications to deter primer dimer formation that allowed amplicon amplification at the lowest target concentration ($10^3$ copies of target per reaction). Using EvaGreen®, a melting curve analysis was done after the PCR provided a qualitative assessment of primer dimer and amplicon formation (FIG. 7-1 and FIG. 7-2) which shows the addition of t, a, c, and g reduces the quantity of useless primer dimer products ($T_m$≈74° C.-79° C.) and increases the quantity of useful amplicon products ($T_m$≈81° C.-84° C.).

Example 5. Primer Dimer and Amplicon Formation with or without MODURA a or t Modification (FIG. 7-1)

Melting transitions after PCR, monitored with intercalated EvaGreen® dye in Example 5, show the primer dimer and PCR amplicon formation with standard primers and primers having t, g, a, and c-modifications in the 3'-overlap region (Table 4-2). In Table 4-2, primer sequences are denoted as fragments, specifically the 5 nt overlap at 3'-ends. For Platinum II Taq, standard primers with perfect 5 nt overlap at their 3' ends: Set A (T:A, SEQ ID NO: 77+SEQ ID NO: 79, FIG. 7-1) produce predominantly primer dimer and essentially no amplicon at medium and low target concentration ($10^4$ and $10^3$ copies of target per reaction). Primers with t modifications (Set B (t:A, SEQ ID NO: 89+SEQ ID NO: 79)) prevent primer dimer formation and produce only PCR amplicon. Primer with a modification: Set C (T:a, SEQ ID NO: 77+SEQ ID NO: 91) generates both primer dimer and PCR amplicon. Primers with t and a modifications: Set D (t:a, SEQ ID NO: 89+SEQ ID NO: 91) produce only PCR amplicon and no signal (NS) for NTC. Both Set B and Set D indicate that t is highly effective at avoiding primer dimer with both Platinum II Taq and Takara RT-PCR kit. These are useful unexpected results.

Example 6. Primer Dimer and Amplicon Formation with/without g or c Modification (FIG. 7-2)

The melting peaks, monitored with intercalated EvaGreen® dye in Example 6, show primer dimer and amplicon formation with standard primers and primers having t, g, a, and c-modifications in the 3'-overlap region (Table 4-2). In Table 4-2, for Platinum II Taq DNA polymerase, standard primers with perfect 5 nt overlaps at their 3'-ends (Set A (C:G, SEQ ID NO: 77+SEQ ID NO: 79)) produce predominantly primer dimer and essentially no amplicon at medium and low target concentration ($10^4$ and $10^3$ copies of target per reaction). Primers with a MODURA c modification (Set E (c:G, SEQ ID NO: 90+SEQ ID NO: 79)) generate both primer dimer and PCR amplicon. Primers with MODURA g modifications (Set F (C:g, SEQ ID NO: 77+SEQ ID NO: 92)) generate both primer dimer and PCR amplicon. Primers with c and g modifications (Set G (c:g, SEQ ID NO: 90+SEQ ID NO: 92)) produce only PCR amplicons, a very useful result. These results indicate that both c and g modifications are required to completely avoiding primer dimers, while t is the most effective component to prevent primer dimers with both Platinum II Taq and Takara RT-PCR kit (FIG. 7-1 and FIG. 7-2).

Table 5. Evaluation of the PCR Efficiency of Standard Primers and t, a, c, and g-Modified Primers Using Target Specific TagMan® Probe To evaluate the PCR efficiency of t, a, c, and g-modified primers, TaqMan® probe was used to monitor the PCR efficiency of two sets of standard primers (Set4-4 and Set5-4 overlap, Table 4-1) and primers having one or two t, a, c, and g modification in the 4 nt overlap region (Table 5-1). All primers were tested in PCR using either Takara RT-PCR kit or Platinum II Taq. PCR efficiency, denoted by Ct, was monitored by target specific TaqMan® probe with different target concentrations ($10^6$, $10^4$, $10^3$ copies of target per reaction, Table 5-1).

In general, standard primers and t, a, c, and g-modified primers gave similar Cts with a standard deviation within 2 cycles for the same target concentrations. One or two t, a, c, and g-modifications (adjacent or separated) in the last four base of a primer do not affect the primer efficiency for both polymerases tested here (Table 5-1). For example, primers with two modifications: SEQ ID NO: 104 (GagG), SEQ ID NO: 106 (CtcC), and SEQ ID NO: 107 (CtCc) had similar Cts as the standard primers (SEQ ID NO: 69 (GAGG), SEQ ID NO: 70 (CTCC)) in TaqMan PCR using both polymerases. Primers with two modifications (SEQ ID NO: 110 (CagA), SEQ ID NO: 113 (GtcT), and SEQ ID NO: 114 (GtCt)) had similar Cts as the standard primers (SEQ ID NO: 82 (CAGA), SEQ ID NO: 84 (GTCT) in TaqMan PCR using Takara RT-PCR kit (Table 5-1).

Figure 8:
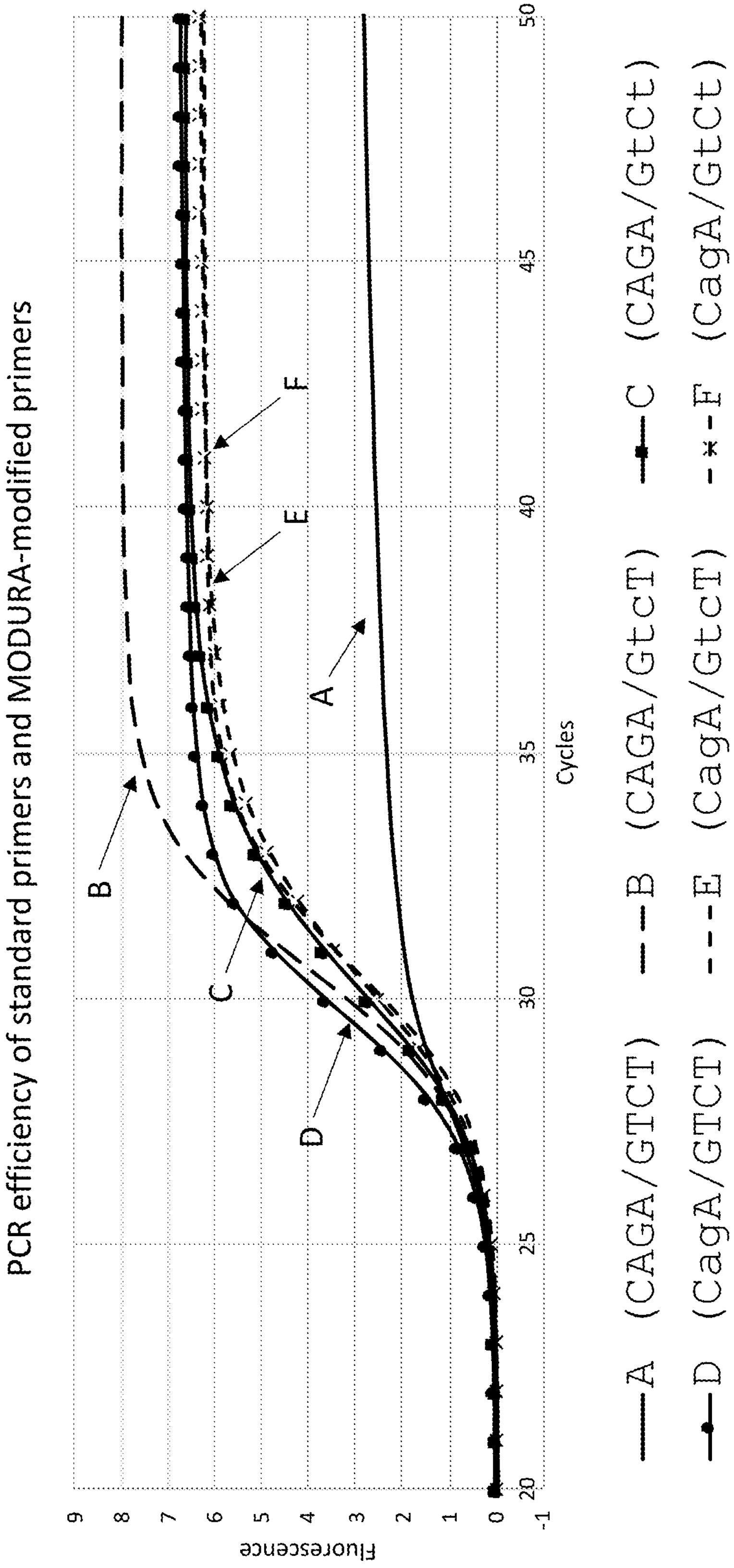
FIG. 8. PCR performance of primers with two t, g, a, and c-modifications using RT-PCR kit with reverse transcriptase (Example 7). PCR efficiency of standard primers and t, g, a, and c-modified primers was monitored by TaqMan® probe in Example 7 and PCR efficiency (Ct) of each primer pair was compared in Table 5-1. Standard primers have a 4 nt overlap at their 3' ends and one or two standard bases are replaced with t, a, c, or g analog in the 4 nt overlap. Two modifications are either adjacent or separated by one standard base (Table 5-1). Example 7 compared the following primer pairs: Set A (standard primers, SEQ ID NO:82+SEQ ID NO:84), Set B (SEQ ID NO:82+SEQ ID NO:113, primer having tc modifications), Set C (SEQ ID NO:82+SEQ ID NO:114, primer having tCt modifications), Set D (primer having ag modifications, SEQ ID NO:110+SEQ ID NO:84), Set E (primer having ag and tc modifications, SEQ ID NO:110+SEQ ID NO:113), and Set F (primer having ag and tCt modifications, SEQ ID NO:110+SEQ ID NO:114). Overall, standard primers and primers having one or two t, g, a, and c-modifications (either adjacent t, g, a, and c or separated by one standard base) have similarly PCR efficiency (Ct with standard deviation less than ~1 Ct for both Takara RT-PCR kit and Platinum II Taq DNA polymerases (Table 5-1). The PCR amplification curve of standard primers monitored by TaqMan probe (Set A, SEQ ID NO:82+SEQ ID NO:84, FIG. 8) has weaker fluorescence intensity than all other primers having t, g, a, and c-modifications. The weaker TaqMan probe signal of standard primers is presumably caused by the consumption of PCR resources to undetected primer dimer artifact.

Example 7. PCR Performance of Primers with Two t, k, a, and c-Modifications Using RT-PCR Kit with Reverse Transcriptase (FIG. 8)

Standard primers having a 4 nt overlap at their 3'-ends were modified with one or two MODURA t, a, c, or g analogs in the 4 nt overlapping region. Two analogs were either adjacent or separated by one standard base (Table 5-1). The PCR efficiency (Ct) of standard primers and t, a, c, and g-modified primers was monitored by TaqMan® probes in Example 7. The Ct of each primer pair was compared in Table 5-1; PCR amplification curves are in FIG. 8. In Example 7 (FIG. 8), following primer pairs were compared: Set A (standard primers, SEQ ID NO:82+SEQ ID NO:84), Set B (SEQ ID NO:82+SEQ ID NO:113, MODURA primer having tc modifications), Set C (SEQ ID NO:82+SEQ ID NO:114, primer having tCt modifications), Set D (primer having ag modifications, SEQ ID NO:110+SEQ ID NO:84), Set E (primer having ag and tc modifications, SEQ ID NO:110+SEQ ID NO:113), and Set F (primer having ag and tCt modifications, SEQ ID NO:110+SEQ ID NO:114). Overall, standard primers and primers having one or two t, g, a, and c-modifications (either adjacent t, g, a, and c or separated by one standard base) have similarly PCR efficiency (Ct with standard deviation less than ~1 Ct for both Takara RT-PCR kit and Platinum II Taq DNA polymerases (Table 5-1). The PCR amplification curve of standard primers monitored by TaqMan probe (Set A, SEQ ID NO:82+SEQ ID NO:84, FIG. 8) has weaker fluorescence intensity than all other primers having t, g, a, and c-modifications. The weaker TaqMan probe signal of standard primers is presumably caused by the consumption of PCR resources to undetected primer dimer artifact.

Standard primers having 5 nt overlaps (SEQ ID NO: 77+SEQ ID NO: 79) and primer modified by a to give a T:a pair in 5 nt overlap (SEQ ID NO: 77+SEQ ID NO: 91) failed to detect target at all concentrations (from $10^6$ to $10^3$ copies of target per reaction) using Takara RT-PCR kit with TaqMan® probe (Table 5-2). Primers modified with one c or g in the 5 nt overlap to give c:G pair (in SEQ ID NO: 90+SEQ ID NO: 79) or C:g pair (in SEQ ID NO: 77+SEQ ID NO: 92) failed to detect target at $10^4$ copies or $10^3$ copies per reaction when using Takara RT-PCR kit (Table 5-2). The failure of target detection is directly related to the formation of primer dimers that suppress the target amplification, as shown in Table 4-2, with PCR assays monitored by EvaGreen® dye; the Ct of the NTC is the same as the Cts of targets from $10^6$ to $10^3$ copies per reaction. In contrast, primer modified with one t to give t:A pair in the 5 nt overlap (SEQ ID NO: 89+SEQ ID NO: 79) and primers having one t:a pair (SEQ ID NO: 89+SEQ ID NO: 91) or one c:g pair in the 5 nt overlap (SEQ ID NO: 90+SEQ ID NO: 92) successfully detected all target with TaqMan probe using Takara RT-PCR kit (Table 5-2).

Standard primers having 6 nt overlap (SEQ ID NO: 85+SEQ ID NO: 87) failed to detect target at all concentrations (from $10^6$ to $10^3$ copies of target per reaction) using target specific TaqMan® probe (Table 5-3), this failure is clearly caused by formation of primer dimer which was shown by non-specific EvaGreen dye with a Ct of 1 cycle when using Takara RT-PCR kit (Table 4-3). Using Platinum II Taq, standard primers were able to detect target at all concentrations using TaqMan probe (Table 5-3), however, fluorescence signal of the amplification curve is much weaker than MODURA-modified primers (FIG. 8). Again, primer dimer was also shown at low target concentration and NTC for PCR with standard primers (SEQ ID NO: 85+SEQ ID NO: 87) using EvaGreen dye (Table 4-3).

Primers having two t, a, c, and g modifications in the 6n overlap region, where modifications can be either adjacent or separated by one or two standard bases, were successful in detecting all targets at all concentrations, with both EvaGreen dye (Table 4-3) and TaqMan probes (Table 5-3). The Cts with TaqMan® probe readouts correlated with EvaGreen® results (Table 5-3 and Table 4-3). The greater the competition between primer dimers and amplicons, particularly when initial template concentrations are low and the overlap footprint are greater than 4 nt, the worse the fluorescent signal and PCR efficiency (Table 4-2 and Table 4-3 vs Table 5-2 and Table 5-3). For example, the standard primers (SEQ ID NO: 77+SEQ ID NO: 79, Table 4-2) gave only primer dimer signal with Takara® using EvaGreen® and there was no signal detected for the same reaction using TaqMan® probe (Table 5-2). In contrast, for primers modified with t, a, c, and g in the 5 nt and 6 nt overlap regions, PCR assays had much higher sensitivity and robust amplification signals using TaqMan probe (Table 5-2 and Table 5-3) and also noted in the results with EvaGreen® (Table 4-2 and Table 4-3).

The ranking of pairs that deter primer dimer formation was discovered to be: t:a >c:g>t:A>C:g≈c:G>T:a or a:t >g:c >A:t >G:c≈g:C >a:T Thus, the presently preferred use of MODURA modifications are as follows:

1. One or two t, a, c, and g components per primer, giving a small decrease of $T_m$ after modification. One t:a or c:g pair is sufficient to deter primer dimers with 4 nt overlaps, with the a:t pair being the most effective. Two complementary a:t and g:c pairs are preferred for preventing primer dimers with 5 nt and 6 nt overlaps. In practical implementation, the presently most preferred strategy replaces, if possible, an A:T pair with an a:t pair, and then replacing a G:C pair with g:c pair in the overlap region.
2. The $T_m$ of the modified primer should be a few degrees higher than annealing temperature used in the PCR. These guidelines are most preferably used in conjunction with established primer dimer design rules.

Table 6. Evaluation of the On-Target and Off-Target PCR Amplification of Standard Primers and MODURA-Modified Primers Primers, designed by software to solve primer dimer problems with standard nucleotides,[14] were modified by t, a, c, and g replacements (Table 6-1 and Table 1-4). Performance of these primers was tested in 96-plex multiplexed PCR. PCR products were sequenced by Illumina deep sequencing and the formation of on-target amplicons and off-target artifacts of the top 6 primer sets was studied and their average NGS coverages (sequencing reads) are provided in Table 6-1. Formation of off-target amplicons with standard primers was also compared with formation of on-target counterparts in single-plex PCR to measure the ratio of off-target to on-target amplicons. Thus, the off-target amplification by T80-Fp and T13-Rp (forward primer for target 80, SEQ ID NO:118 and reverse primer for target 13, SEQ ID NO: 119, Table 6-1) was compared to the on-target amplification by T80-Fp and T80-Rp (on-target 80, SEQ ID NO:118+120) and T13-Fp and T13-Rp (on-target 13, SEQ ID NO: 121+119). The results showed that most off-target sets in Table 6-1 gave earlier Ct than on-target counterparts (Table 6-2).

To show the benefit of t, a, c, and g modifications in improving the on-versus off-target amplicon ratios, primers were modified with t, a, c, and g. As Table 6-2 shows, a 3 to 9 cycles of Ct delay in the generation of off-target amplicons was seen, comparing modified primers with standard primers. This indicates a 10- to 1000-fold reduction in off-target formation by modified primers, a surprising and highly useful result.

On-target amplification of standard and t, a, c, and g-modified primers was then compared. The data discovered that modified primers are superior to natural standard primers in producing more on-target products with a single and sharp melting peaks for each target, while standard primers exhibit broad, multi-peak curves that indicate a consumption of PCR resources by substantial amounts of off-target amplicons (FIG. 9).

As conclusions to guide the practice of the MODURA invention:

1. Interactions between t, a, c, and g with standard nucleotides (t:A, g:C, c:G, tg:AC, tc:AG, etc. pairs) deterring primer dimer formation arising from pairs with four-nucleotide and five-nucleotide overlaps (Table 4, Table 5, FIG. 7-1, and FIG. 7-2). These modifications can be used as a way to prevent primers from interacting with extraneous DNA and RNA that might be present in a sample (Table 6 and FIG. 9)
2. Compared to standard primers, t, a, c, and g-modified primers delay off-target amplification by about 3 to 9 cycles, a 10- to 1000-fold of reduction of off-target formation by t, a, c, andg primers (Table 6-2).
3. PCR efficiency of on-target amplification is either negligibly affected (1-2 cycle delay) or enhanced by t, a, c, and g modification (faster by 4-9 cycles) (Table 6-2). Indicating successful on-target amplification, single sharp melting is seen with t, a, c, and g-modified primers, not with standard primers, which have weak broad peaks (FIG. 9).

Example 8. Evaluating the Effectiveness of t, a, c, and g Modifications in Preventing Off-Target Amplification (FIG. 9)

In Example 8 (FIG. 9), each pair of standard primers or t, a, c, and g-modified primers were tested in PCR that targeted sequences within a sample of human genomic DNA. PCR amplification was monitored by EvaGreen® dye. The final PCR products were identified by melting. Four pairs of standard primers in FIG. 9 (left) are Set 7 (T80, SEQ ID NO: 118+SEQ ID NO: 120), Set 8 (T57, SEQ ID NO: 125+SEQ ID NO: 123), Set 9 (T93, SEQ ID NO: 127+SEQ ID NO: 126), and Set 10 (T11, SEQ ID NO: 128+SEQ ID NO: 130). Four pairs of t, a, c, and g-modified primers in FIG. 9 (right) are Set 7 (T80, SEQ ID NO: 132+SEQ ID NO: 134), Set 8 (T57, SEQ ID NO: 139+SEQ ID NO: 137), Set 9 (T93, SEQ ID NO: 141+SEQ ID NO: 140), and Set 10 (T11, SEQ ID NO: 142+SEQ ID NO: 144). All standard primers were designed by the state-of-the-art bioinformatic software[14] to avoid primer dimer formation. The results (FIG. 9, Table 6-2) show that the designed standard primers generate significantly off-targeting amplicons (multiple melting peaks in FIG. 9 left). In contrast, t, a, c, and g-modified primers produce only the desired PCR amplicon (single melting peak in FIG. 9 right).

Example 9. Making Alkenyl and Alkynyl Variants with Tags (FIG. 10)

To a stirred solution of 18 (260 mg, 0.77 mmol) in DMF (10 mL) is added CuI (30 mg, 0.16 mmol), $Pd(PPh_3)_4$ (86 mg, 0.077 mmol), $Et_3N$ (0/27 mL, 1.9 mmol) and trifluoroacetyl-1-aminobut-3-ene (3.08 mmol) at room temperature. The reaction mixture is stirred overnight at room temperature and evaporated. The residue is purified by silica gel column chromatography to give 19a. The trifluoroacetic acid group can be removed in mild base to allow subsequent derivatization, including derivatization with tagging groups such as biotin or fluorophores.

Alternatively, to a stirred solution of 18 (260 mg, 0.77 mmol) in DMF (10 mL) is added CuI (30 mg, 0.16 mmol), $Pd(PPh_3)_4$ (86 mg, 0.077 mmol), $Et_3N$ (0/27 mL, 1.9 mmol) and trifluoroacetyl-1-aminobut-3-yne (3.08 mmol) at room temperature. The reaction mixture is stirred overnight at room temperature and evaporated. The residue is purified by silica gel column chromatography to give 19a. The trifluoroacetic acid group can be removed in mild base to allow subsequent derivatization, including derivatization with tagging groups such as biotin or fluorophores.

REFERENCES

[1] R. K. Saiki, D. H. Gelfand, S. Stoffel, S. J. Scharf, R. Higuchi, G. T. Horn, K. B. Mullis, H. A. Erlich (1988) Primer-directed enzymatic amplification of DNA with a thermostable DNA polymerase. *Science,* 239, 487-491.

[2] Hoshika, S., Leal, N., Chen, F., Benner, S. A. (2010) Artificial genetic systems. Self-avoiding DNA in PCR and multiplexed PCR. *Angew. Chem. Int. Edit,* 49, 5554-5557.

[3] Yang, Z., Le, J. T., Hutter, D., Bradley, K. M., Overton, B., McLendon, D. C., Benner, S. A. (2020) Eliminating primer dimers and improving SNP detection using self-avoiding molecular recognition systems. Biology Methods and Protocols. 5(1), 1-13

[4] Sharma, N., Hoshika, S., Hutter, D., Bradley, K. M. and Benner, S. A. (2014) Recombinase-Based Isothermal Amplification of Nucleic Acids with Self-Avoiding Molecular Recognition Systems. ChemBioChem, 15, 2268-2274. doi: 10.1002/cbic.201402250

[5] Yang, Z., McLendon, C., Hutter, D., Bradley, K. M., Frye, C., Benner, S. A. (2015) Helicase dependent isothermal amplification of DNA and RNA using self-avoiding molecular recognition systems. ChemBioChem, 16, 1365-1370.

[6] Glushakova, L. G., Bradley, A., Bradley. K. M., Alto, B. W., Hoshika, S., Hutter, D., Sharma, N., Yang, Benner, S. A. (2015) High-throughput multiplexed xMAP Luminex array panel for detection of twenty two medically important mosquito-borne arboviruses based on innovations in synthetic biology. *J. Virol. Meth.,* 214, 60-74.

[7] Alanio, A. and Bretagne, S. (2017) Performance evaluation of multiplex PCR including *Aspergillus*—not so simple-!*Medical Mycology,* 55, 56-62.

[8] Benner, S. A. (2016) Self-avoiding molecular recognition systems in DNA priming. U.S. Pat. No. 9,249,458.

[9] Lan, T., McLaughlin, L. W. (2000) Minor groove hydration is critical to the stability of DNA duplexes. *J. Am. Chem. Soc.* 122(27), 6512-6513.

[10] Lan, T., McLaughlin, L. W. (2001) Minor groove functional groups are critical for the B-form conformation of duplex DNA. *Biochemistry,* 40(4), 968-976.

[11] Froehler, B. C., Gutierrez, A. J., Matteucci, M. D. (2002) 3-Aminopyridine and 2-pyridone C-nucleosides, oligonucleotides comprising, and tests using the same oligonucleotides. U.S. Pat. No. 6,447,998.

[12] Yang, Z., Hutter, S., Sheng, P., Sismour, A. M., Steven A. Benner, S. A. (2006) Artificially expanded genetic information system: a new base pair with an alternative hydrogen bonding pattern. *Nucleic Acids Research,* 34(21), 6095-6101.

[13] Yang, Z., Chen, F., Chamberlin, S. G., & Benner, S. A. (2010). Expanded genetic alphabets in the polymerase chain reaction. Angewandte Chemie (International Ed. in English), 49(1), 177.

[14] Xie, N. G., Wang, M. X., Song, P., Mao, S., Wang, Y., Yang, Y., Luo, J., Ren, S., Zhang, D. Y. (2022) Designing highly multiplex PCR primer sets with Simulated Annealing Design using Dimer Likelihood Estimation (SADDLE). *Nature Commun.* 13, 1881.

What is claimed is:

1. A compound selected from the group consisting of:

(a) a compound having the structure

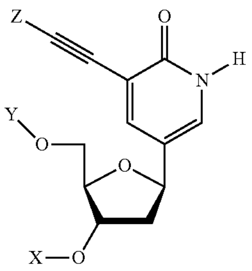

or

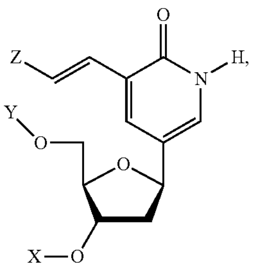

wherein (i) Z attached to the alkenyl linker attached to the substituted pyridone heterocycle is either H, $CH_3$, an alkyl group that is not $CH_3$, or an alkyl group carrying a tag, or (ii) Z attached to the alkynyl linker attached to the substituted pyridone heterocycle is either H, $CH_3$, an alkyl group that is not $CH_3$, or an alkyl group carrying a tag, and (iii) Y is independently H, phosphate, diphosphate, or triphosphate, a protecting group, or a phosphoramidite group, and (iv) X is independently H, phosphate, diphosphate, or triphosphate, a protecting group, or a phosphoramidite group; and (b) a compound having the structure

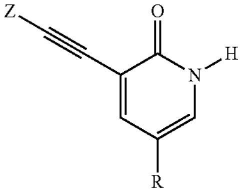

or

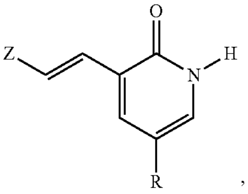

, wherein (i) Z attached to the alkenyl linker attached to the substituted pyridone heterocycle is either H, $CH_3$, an alkyl group that is not $CH_3$, or an alkyl group carrying a tag; or (ii) Z attached to the alkynyl linker attached to the substituted pyridone heterocycle is either H, $CH_3$, an alkyl group that is not $CH_3$, or an alkyl group carrying a tag; and (iii) R is a sugar ring.

2. The compound according to claim 1, wherein in (a) the compound has the structure

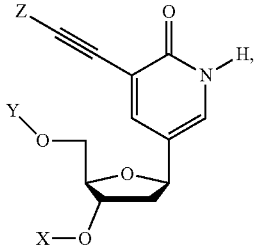

wherein Z attached to the alkynyl linker attached to the substituted pyridone heterocycle is $CH_3$; Y is independently H, phosphate, diphosphate, or triphosphate, a protecting group, or a phosphoramidite group; and X is independently H, phosphate, diphosphate, or triphosphate, a protecting group, or a phosphoramidite group; or in (b) the compound has the structure

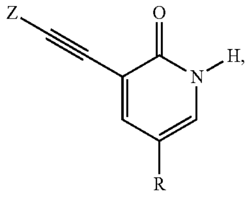

wherein Z attached to the alkynyl linker attached to the substituted pyridone heterocycle is $CH_3$; and R is a sugar ring.

3. The compound according to claim 1, wherein in (a) the compound has the structure

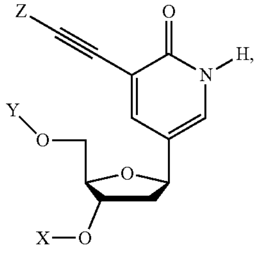

wherein Z attached to the alkynyl linker attached to the substituted pyridone heterocycle is H, an alkyl group that is not $CH_3$, or an alkyl group carrying a tag; Y is independently H, phosphate, diphosphate, or triphosphate, a protecting group, or a phosphoramidite group; and X is independently H, phosphate, diphosphate, or triphosphate, a protecting group, or a phosphoramidite group; or in (b) the compound has the structure

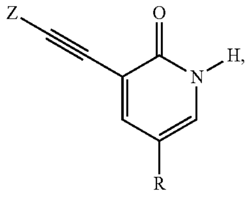

wherein Z attached to the alkynyl linker attached to the substituted pyridone heterocycle is H, $CH_3$, an alkyl group that is not $CH_3$, or an alkyl group carrying a tag; and R is a sugar ring.

4. The compound according to claim 1, wherein in (a) the compound has the structure

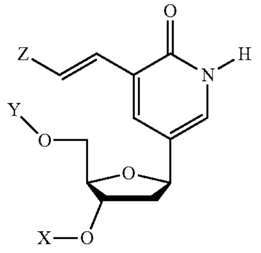

wherein Z attached to the alkenyl linker attached to the substituted pyridone heterocycle is H, $CH_3$, an alkyl group that is not $CH_3$, or an alkyl group carrying a tag; Y is independently H, phosphate, diphosphate, or triphosphate, a protecting group, or a phosphoramidite group, and X is independently H, phosphate, diphosphate, or triphosphate, a protecting group, or a phosphoramidite group; or in (b) the compound has the structure

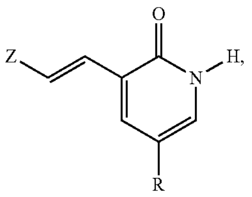

wherein Z attached to the alkenyl linker attached to the substituted pyridone heterocycle is H, $CH_3$, an alkyl group that is not $CH_3$, or an alkyl group carrying a tag; and R is a sugar ring.

5. An oligonucleotide analog, wherein one or more of the nucleotide units has, instead of one or more standard nucleobases, a substituted heterocycle that has the structure

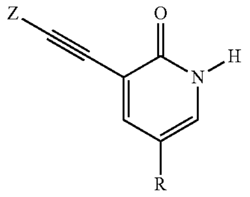

or

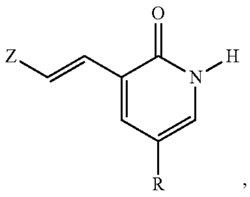

, wherein (i) Z attached to the alkenyl linker attached to the substituted pyridone heterocycle is either H, $CH_3$, an alkyl group that is not $CH_3$, or an alkyl group carrying a tag; or (ii) Z attached to the alkynyl linker attached to the substituted pyridone heterocycle is either H, $CH_3$, an alkyl group that is not $CH_3$, or an alkyl group carrying a tag;

wherein R is the point of attachment of said substituted heterocycle to the remainder of said oligonucleotide analog.

6. The oligonucleotide analog according to claim 5, wherein one or more of the nucleotide units has, instead of one or more standard nucleobases, a substituted heterocycle that has the structure

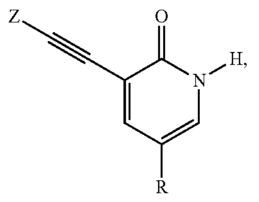

wherein Z attached to the alkynyl linker attached to the substituted pyridone heterocycle is $CH_3$; wherein R is the point of attachment of said substituted heterocycle to the remainder of said oligonucleotide analog.

7. The oligonucleotide analog according to claim 5, wherein one or more of the nucleotide units has, instead of one or more standard nucleobases, a substituted heterocycle that has the structure

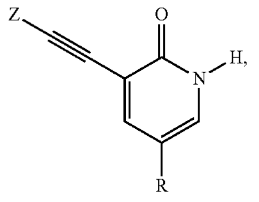

wherein Z attached to the alkynyl linker attached to the substituted pyridone heterocycle is H, an alkyl group that is not $CH_3$, or an alkyl group carrying a tag; wherein R is the point of attachment of said substituted heterocycle to the remainder of said oligonucleotide analog.

8. The oligonucleotide analog according to claim 5, wherein one or more of the nucleotide units has, instead of one or more standard nucleobases, a substituted heterocycle that has the structure

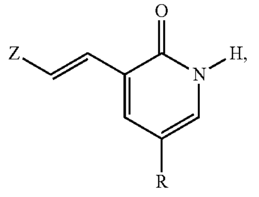

wherein Z attached to the alkenyl linker attached to the substituted pyridone heterocycle is H, $CH_3$, an alkyl group that is not $CH_3$, or an alkyl group carrying a tag; wherein R is the point of attachment of said substituted heterocycle to the remainder of said oligonucleotide analog.

9. The oligonucleotide analog according to claim 5, wherein said oligonucleotide analog in addition also has, instead of one or more standard nucleobases, one or more heterocycles selected from the group consisting of N-methylcytosine, N-ethylcytosine, 2-aminopurine, 2,6-diaminopurine, and hypoxanthine.

10. The oligonucleotide analog according to claim 6, wherein said oligonucleotide analog in addition also has, instead of one or more standard nucleobases, one or more heterocycles selected from the group consisting of N-methylcytosine, N-ethylcytosine, 2-aminopurine, 2,6-diaminopurine, and hypoxanthine.

11. The oligonucleotide analog according to claim 7, wherein said oligonucleotide analog in addition also has, instead of one or more standard nucleobases, one or more heterocycles selected from the group consisting of N-methylcytosine, N-ethylcytosine, 2-aminopurine, 2,6-diaminopurine, and hypoxanthine.

12. The oligonucleotide analog according to claim 8, wherein said oligonucleotide analog in addition also has, instead of one or more standard nucleobases, one or more heterocycles selected from the group consisting of N-methylcytosine, N-ethylcytosine, 2-aminopurine, 2,6-diaminopurine, and hypoxanthine.

13. A composition comprising a compound according to claim 1 and a buffer.

14. The composition according to claim 13, wherein in (a) the compound has the structure

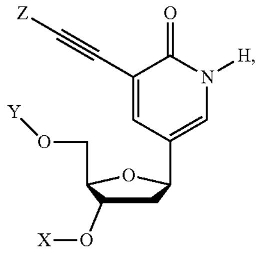

wherein Z attached to the alkynyl linker attached to the substituted pyridone heterocycle is $CH_3$; Y is independently H, phosphate, diphosphate, or triphosphate, a protecting group, or a phosphoramidite group; and X is independently H, phosphate, diphosphate, or triphosphate, a protecting group, or a phosphoramidite group; or in (b) the compound has the structure

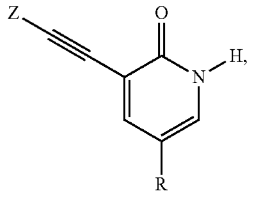

wherein Z attached to the alkynyl linker attached to the substituted pyridone heterocycle is $CH_3$; and R is a sugar ring.

15. The composition according to claim 13, wherein in (a) the compound has the structure

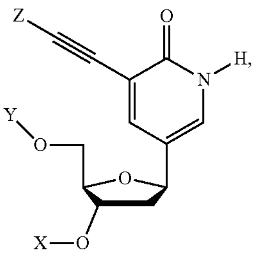

wherein Z attached to the alkynyl linker attached to the substituted pyridone heterocycle is H, an alkyl group that is not $CH_3$, or an alkyl group carrying a tag; Y is independently H, phosphate, diphosphate, or triphosphate, a protecting group, or a phosphoramidite group;

and X is independently H, phosphate, diphosphate, or triphosphate, a protecting group, or a phosphoramidite group; or in (b) the compound has the structure

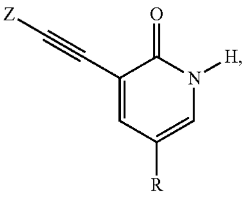

wherein Z attached to the alkynyl linker attached to the substituted pyridone heterocycle is H, an alkyl group that is not $CH_3$, or an alkyl group carrying a tag; and R is a sugar ring.

16. The composition according to claim 13, wherein in (a) the compound has the structure

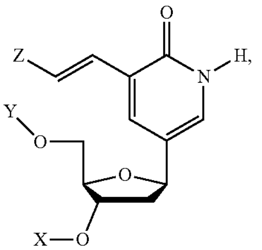

wherein Z attached to the alkenyl linker attached to the substituted pyridone heterocycle is H, $CH_3$, an alkyl group that is not $CH_3$, or an alkyl group carrying a tag; Y is independently H, phosphate, diphosphate, or triphosphate, a protecting group, or a phosphoramidite group; and X is independently H, phosphate, diphosphate, or triphosphate, a protecting group, or a phosphoramidite group; or in (b) the compound has the structure

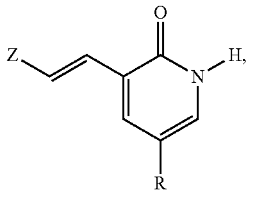

wherein Z attached to the alkenyl linker attached to the substituted pyridone heterocycle is H, $CH_3$, an alkyl group that is not $CH_3$, or an alkyl group carrying a tag; and R is a sugar ring.

17. A composition comprising at least one oligonucleotide analog according to claim 5 and a buffer.

18. The composition according to claim 17, wherein the at least one oligonucleotide analog has the structure

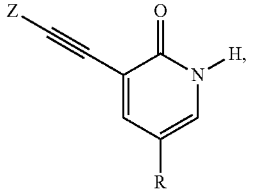

wherein Z attached to the alkynyl linker attached to the substituted pyridone heterocycle is $CH_3$; wherein R is the point of attachment of said substituted heterocycle to the remainder of said oligonucleotide analog.

19. The composition according to claim 17 wherein the at least one oligonucleotide analog has the structure

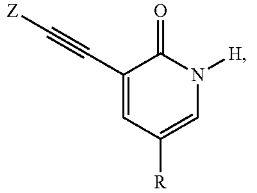

wherein Z attached to the alkynyl linker attached to the substituted pyridone heterocycle is H, an alkyl group that is not $CH_3$, or an alkyl group carrying a tag; wherein R is the point of attachment of said substituted heterocycle to the remainder of said oligonucleotide analog.

20. The composition according to claim 17, wherein the at least one oligonucleotide analog has the structure

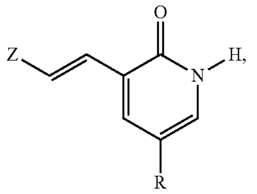

wherein Z attached to the alkenyl linker attached to the substituted pyridone heterocycle is H, $CH_3$, an alkyl group that is not $CH_3$, or an alkyl group carrying a tag; wherein R is the point of attachment of said substituted heterocycle to the remainder of said oligonucleotide analog.

21. The composition according to claim 17, wherein said oligonucleotide analog in addition also has, instead of one or more standard nucleobases, one or more heterocycles selected from the group consisting of N-methylcytosine, N-ethylcytosine, 2-aminopurine, 2,6-diaminopurine, and hypoxanthine.

22. The composition according to claim 18, wherein said oligonucleotide analog in addition also has, instead of one or more standard nucleobases, one or more heterocycles selected from the group consisting of N-methylcytosine, N-ethylcytosine, 2-aminopurine, 2,6-diaminopurine, and hypoxanthine.

23. The composition according to claim 19, wherein said oligonucleotide analog in addition also has, instead of one or more standard nucleobases, one or more heterocycles selected from the group consisting of N-methylcytosine, N-ethylcytosine, 2-aminopurine, 2,6-diaminopurine, and hypoxanthine.

24. The composition according to claim 17, further comprising at least one additional oligonucleotide analog that has, instead of one or more standard nucleobases, one or more heterocycles independently selected from the group consisting of N-methylcytosine, N-ethylcytosine, 2-aminopurine, 2,6-diaminopurine, hypoxanthine,

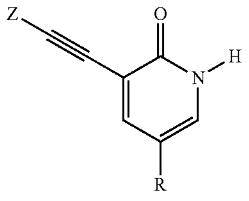

and

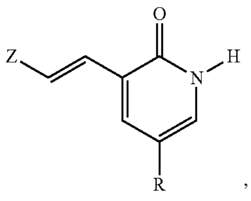

, wherein (A) Z attached to the alkenyl linker attached to the substituted pyridone heterocycle is either H, $CH_3$, an alkyl group that is not $CH_3$, or an alkyl group carrying a tag; or (B) Z attached to the alkynyl linker attached to the substituted pyridone heterocycle is either H, $CH_3$, an alkyl group that is not $CH_3$, or an alkyl group carrying a tag;

wherein R is the point of attachment of said substituted heterocycle to the remainder of said oligonucleotide analog.

25. The composition according to claim 24, wherein in (A) Z attached to the alkenyl linker attached to the substituted pyridone heterocycle is H, $CH_3$, an alkyl group that is not $CH_3$, or an alkyl group carrying a tag; wherein R is the point of attachment of said substituted heterocycle to the remainder of said oligonucleotide analog.

26. The composition according to claim 24, wherein in (B) Z attached to the alkynyl linker attached to the substituted pyridone heterocycle is $CH_3$; wherein R is the point of attachment of said substituted heterocycle to the remainder of said oligonucleotide analog.

27. The composition according to claim 24, wherein in (B) Z attached to the alkynyl linker attached to the substituted pyridone heterocycle is H, an alkyl group that is not $CH_3$, or an alkyl group carrying a tag; wherein R is the point of attachment of said substituted heterocycle to the remainder of said oligonucleotide analog.

28. A process for making a compound according to claim 1, the process comprising:

(i) providing 2-bromo-5-iodopyridine;

(ii) reacting 2-bromo-5-iodopyridine with benzyl alcohol to obtain 2-BnOH-5-pyridine;

(iii) adding 4,5-dihydro-4-(tertiarybutyl-disilyloxy)-5-hydroxymethyltetrahydrofuran, a catalyst and an ancillary ligand to 2-BnOH-5-pyridine to obtain 2-BnOH-3-iodo-5-pyridine-ribofuranose derivative; and (iv) reacting 2-BnOH-3-iodo-5-pyridine-ribofuranose derivative with an alkynyl or an alkenyl to obtain a compound having the structure

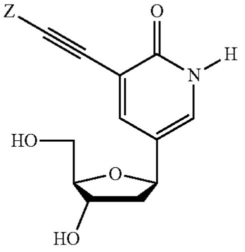

or

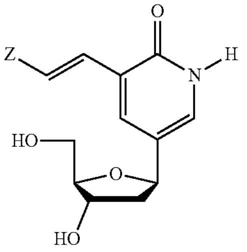

wherein (i) Z attached to the alkenyl linker attached to the substituted pyridone heterocycle is either H, $CH_3$, an alkyl group that is not $CH_3$, or an alkyl group carrying a tag, or (ii) Z attached to the alkynyl linker attached to the substituted pyridone heterocycle is either H, $CH_3$, an alkyl group that is not $CH_3$, or an alkyl group carrying a tag.

29. The process according to claim 28, wherein in (i) Z attached to the alkenyl linker attached to the substituted pyridone heterocycle is H, $CH_3$, an alkyl group that is not $CH_3$, or an alkyl group carrying a tag.

30. The process according to claim 28 wherein in (ii) Z attached to the alkynyl linker attached to the substituted pyridone heterocycle is $CH_3$.

31. The process according to claim 28, wherein in (ii) Z attached to the alkynyl linker attached to the substituted pyridone heterocycle is H, an alkyl group that is not $CH_3$, or an alkyl group carrying a tag.

* * * * *